US012711620B2

(12) United States Patent
Natarajan et al.

(10) Patent No.: US 12,711,620 B2
(45) Date of Patent: Aug. 18, 2026

(54) CANCER MAPPING USING MACHINE LEARNING

(71) Applicant: Avenda Health, Inc., Santa Monica, CA (US)

(72) Inventors: Shyam Natarajan, Los Angeles, CA (US); Alan Martin Priester, Mission Viejo, CA (US); Joshua Dylan Shubert, Los Angeles, CA (US); Jeremy Tet Kong Bong, Santa Monica, CA (US); Brittany Nan Pusey, Seattle, WA (US)

(73) Assignee: AVENDA HEALTH, INC., Culver City, CA (US)

( * ) Notice: Subject to any disclaimer, the term of this patent is extended or adjusted under 35 U.S.C. 154(b) by 292 days.

(21) Appl. No.: 18/473,101

(22) Filed: Sep. 22, 2023

(65) Prior Publication Data

US 2024/0105311 A1 Mar. 28, 2024

Related U.S. Application Data

(60) Provisional application No. 63/376,938, filed on Sep. 23, 2022, provisional application No. 63/385,757, filed on Dec. 1, 2022.

(51) Int. Cl.
*G06T 7/00* (2017.01)
*A61B 6/46* (2024.01)
(Continued)

(52) U.S. Cl.
CPC ............ *G06T 7/0012* (2013.01); *A61B 6/469* (2013.01); *G16H 30/20* (2018.01); *G16H 30/40* (2018.01);
(Continued)

(58) Field of Classification Search
CPC .................... G06T 7/0012; G06T 7/11; G06T 2207/10088; G06T 2207/20081;
(Continued)

(56) References Cited

U.S. PATENT DOCUMENTS

| | | | | |
|---|---|---|---|---|
| 7,844,087 | B2 * | 11/2010 | Ray | G06T 7/0012 382/128 |
| 8,280,133 | B2 * | 10/2012 | Wels | G06T 7/11 382/128 |

(Continued)

FOREIGN PATENT DOCUMENTS

| | | | |
|---|---|---|---|
| WO | 2020205204 | A1 | 10/2020 |
| WO | 2022053817 | A1 | 3/2022 |
| WO | 2022099303 | A1 | 5/2022 |

OTHER PUBLICATIONS

Bi, Wenya Linda, et al. "Artificial intelligence in cancer imaging: clinical challenges and applications." CA: a cancer journal for clinicians 69(2), pp. 127-157 (Year: 2019).*

(Continued)

*Primary Examiner* — Scott A Rogers
(74) *Attorney, Agent, or Firm* — Dorsey & Whitney LLP

(57) ABSTRACT

A method for mapping cancer includes inputting data elements from medical images, biopsy, and biopsy pathology labels into a machine learning model estimating the likelihood of clinically significant cancer in a patient and outputting, via the machine learning model, an estimate of the clinically significant cancer likelihood at each voxel of a three-dimensional image.

19 Claims, 33 Drawing Sheets

(51) Int. Cl.
*G06T 7/11* (2017.01)
*G16H 30/20* (2018.01)
*G16H 30/40* (2018.01)
*G16H 50/20* (2018.01)
*G16H 50/30* (2018.01)

(52) U.S. Cl.
CPC ............. *G16H 50/20* (2018.01); *G16H 50/30* (2018.01); *G06T 7/11* (2017.01); *G06T 2207/10088* (2013.01); *G06T 2207/20081* (2013.01); *G06T 2207/20084* (2013.01); *G06T 2207/30081* (2013.01); *G06T 2207/30096* (2013.01)

(58) Field of Classification Search
CPC . G06T 2207/20084; G06T 2207/30081; G06T 2207/30096; G16H 30/20; G16H 30/40; G16H 50/20; G16H 50/30; A61B 5/7475; A61B 5/748; A61B 5/7485; A61B 6/467; A61B 6/469; A61B 8/467; A61B 8/469
See application file for complete search history.

(56) References Cited

U.S. PATENT DOCUMENTS

| | | | | |
|---|---|---|---|---|
| 8,379,950 | B2 * | 2/2013 | Ye | G06T 7/0012 382/128 |
| 8,908,948 | B2 * | 12/2014 | Fan | G06T 7/143 382/128 |
| 8,970,578 | B2 * | 3/2015 | Voros | A61B 6/504 382/128 |
| 9,129,382 | B2 * | 9/2015 | Fan | G06T 7/162 |
| 10,603,007 | B2 * | 3/2020 | Zhang | A61B 8/4455 |
| 11,341,640 | B2 | 5/2022 | Enzmann et al. | |
| 11,701,066 | B2 * | 7/2023 | Yan | G06F 18/21 382/131 |
| 11,721,428 | B2 * | 8/2023 | Brynolfsson | G16H 50/30 382/131 |
| 12,417,533 | B2 * | 9/2025 | Anand | G16H 50/20 |
| 2012/0008838 | A1 | 1/2012 | Guyon et al. | |
| 2020/0342600 | A1 | 10/2020 | Sjöstrand et al. | |
| 2022/0059227 | A1 * | 2/2022 | Park | G06T 7/13 |
| 2022/0138949 | A1 * | 5/2022 | Enzmann | G06T 7/0016 382/128 |
| 2023/0410301 | A1 * | 12/2023 | Rajagopal | A61B 5/055 |
| 2024/0354940 | A1 * | 10/2024 | Sjöstrand | G16H 30/40 |

OTHER PUBLICATIONS

He, Mingze, et al. "Research progress on deep learning in magnetic resonance imaging based diagnosis and treatment of prostate cancer: a review on the current status and perspectives." Frontiers in oncology 10: 3389, pp. 1-14 (Year: 2023).*

Rabaan, Ali A., et al. "Artificial intelligence for clinical diagnosis and treatment of prostate cancer." MDPI Cancers 14: 5595, pp. 1-23 (Year: 2022).*

Tătaru, O. S., et al. "Artificial intelligence and machine learning in prostate cancer patient management—Current trends and future perspectives." MDPI Diagnostics 11: 354, pp. 1-20 (Year: 2021).*

Olawuyi, Olushola, and Serestina Viriri. "Deep Learning Techniques for Prostate Cancer Analysis and Detection: Survey of the State of the Art." Journal of Imaging 11(8), p. 254. (Year: 2025).*

International Search Report and Written Opinion dated Jan. 2, 2024 for PCT/US2023/074951.

EP23869253.7 Extended European Search Report dated Sep. 25, 2025.

* cited by examiner

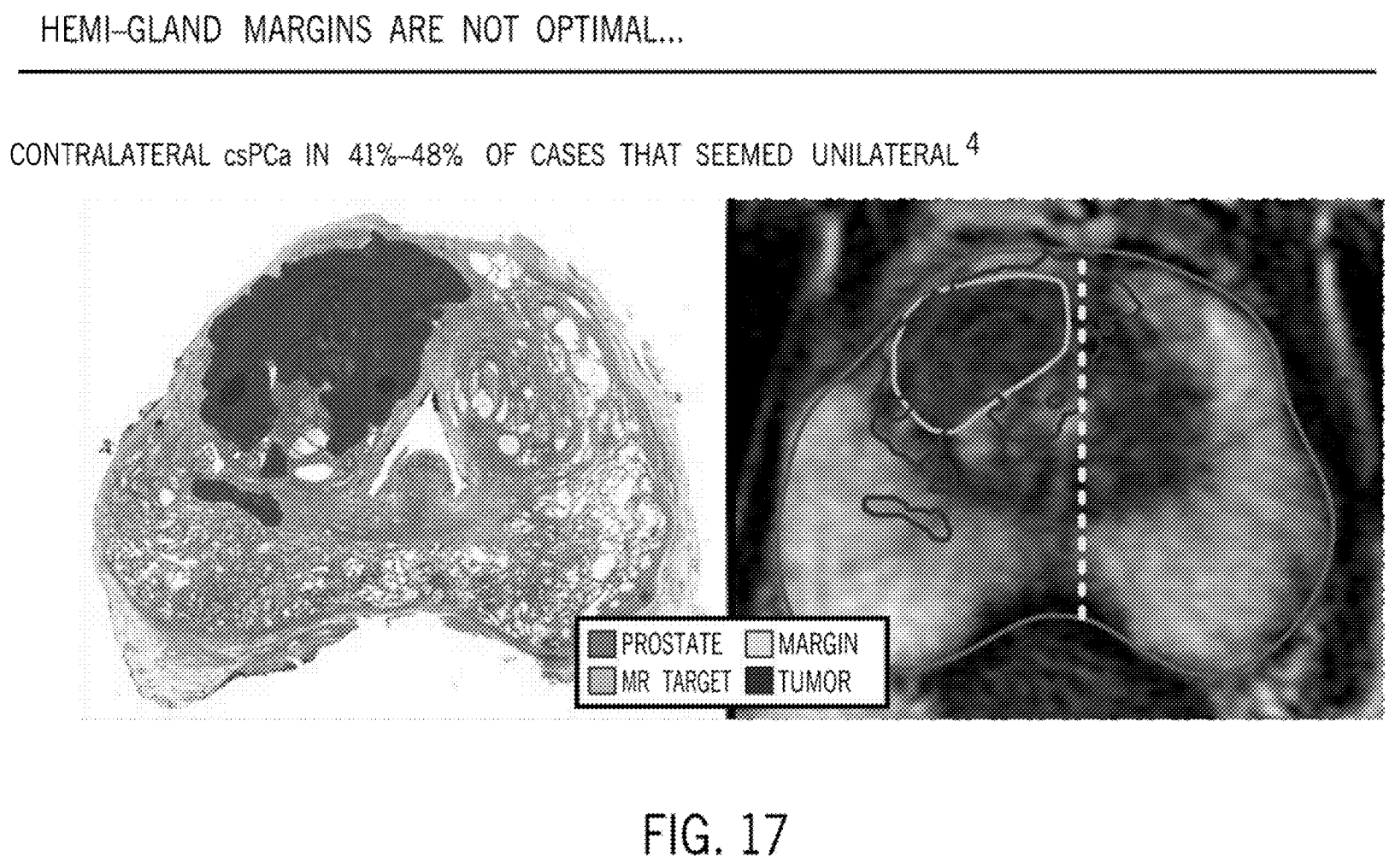

HEMI-GLAND MARGINS ARE NOT OPTIMAL...

CONTRALATERAL csPCa IN 41%–48% OF CASES THAT SEEMED UNILATERAL [4]

PROSTATE
MARGIN
MR TARGET
TUMOR

FIG. 17

ISOTROPIC ROI EXPANSION IS NOT OPTIMAL...

CANCER TENDS TO EXTEND ASYMMETRICALLY BEYOND THE ROI 3

CANCER MAPPING USING MACHINE LEARNING

CROSS-REFERENCE TO RELATED APPLICATION

This application claims priority to U.S. Provisional Patent Application Nos. 63/376,938 filed on Sep. 23, 2022 and 63/385,757 filed on Dec. 1, 2022, the disclosure of each of which is incorporated herein, in its entirety, by this reference.

TECHNICAL FIELD

The present disclosure generally relates to systems and methods for detecting cancerous lesions. More particularly, the present disclosure relates to systems and methods of identifying cancerous lesions using machine learning algorithms.

BACKGROUND

Traditionally, the general location of cancer within an organ or other human tissue is identified with medical imaging technologies such as magnetic resonance imaging (MRI) and treated with surgery, radiation therapy, chemotherapy, hormone therapy, and/or other methods. Many of these treatment therapies can cause harm to healthy tissue of the organ or healthy tis sue surrounding the cancerous tissue, causing irreparable and unnecessary damage if introduced to areas other than the cancerous region(s). It can be difficult for a physician to precisely predict the extent of cancerous tissue within a region, including determining a precise boundary between cancerous cells and healthy tissue. Often times, the physician must over-estimate the size of a cancerous lesion to ensure all cancer cells are removed, to the detriment of some surrounding healthy tissue also being removed. However, depending on the size of the cancerous lesion and the size of the organ in which the cancer is present, this removal of healthy tissue can be detrimental to the continuing function of the organ.

One example of such an organ is the prostate, a small ellipsoid-shaped gland in males that produces seminal fluid. Prostate cancer, after skin cancer, is the most common cancer among men. Prostate cancer can be detected at the local or regional stages, which represent stages I, II and III. The location and anatomy of the prostate makes treatment of cancerous lesions on or within the prostate difficult, often time damaging regions of the prostate or adjacent organs other than the cancerous lesion.

For this and other reasons, there is a need for improvements in the field of detecting and characterizing cancerous lesions on or within a prostate.

SUMMARY

In at least one example of the present disclosure, a device for mapping cancer can include a processor electrically coupled to a memory component storing electronic instructions that, when executed by the processor, causes the device to execute a machine learning algorithm configured to receive inputs and produce an output based on the inputs, wherein the inputs include data elements from a medical image and the output includes an estimate of clinically significant cancer likelihood at each voxel of a three-dimensional image.

In one example, the inputs further include prostate specific antigen (PSA) and the clinically significant cancer likelihood includes clinically significant prostate cancer (csPCa) likelihood. In one example, the output further includes a cancer estimation map (CEM). In one example, the CEM illustrates a color-coded heat map representing a likelihood of cancer at each voxel of the three-dimensional image. In one example, the medical image is an MRI image of a patient's anatomy. In one example, the anatomy includes a prostate. In one example, the CEM includes a lesion contour representing a lesion size of a cancer lesion shown in the three-dimensional image. In one example, the output further includes a visual curve representing an encapsulation confidence score versus the lesion size. In one example, the visual curve includes a point representing a certain lesion size and a certain encapsulation confidence score. In one example, the point is configured to be visually manipulated along the visual curve to change the certain lesion size and the certain encapsulation confidence score represented by the point, wherein manipulating the point alters the lesion contour.

In at least one example of the present disclosure, a method for mapping cancer includes inputting data elements from medical images into a machine learning model estimating the likelihood of clinically significant cancer in a patient and outputting, via the machine learning model, an estimate of the clinically significant cancer likelihood at each voxel of a three-dimensional image.

In one example, the method further includes inputting a prostate specific antigen (PSA) data element into the machine learning model. In one example, the machine learning model is trained on a population dataset including the data elements. In one example, the output includes a visual representation of the three-dimensional image with a color-coded heat map representing the clinically significant cancer likelihood at each voxel.

In at least one example of the present disclosure, a method for mapping cancer includes inputting data elements from medical images into a machine learning model estimating the likelihood of clinically significant cancer in a patient and displaying a visual representation of an estimate of the clinically significant cancer likelihood at each voxel of a three-dimensional image. The visual representation can include a cancer estimation map (CEM) illustrating a color-coded heat map representing a likelihood of clinically significant cancer lesion overlying the image, the CEM including a lesion contour representing the size of the cancer lesion and a curve representing an encapsulation confidence score versus the size, the curve including a point representing the lesion size and the encapsulation confidence score. In such an example, the point is configured to be visually manipulated along the curve to change the lesion size and the encapsulation confidence score represented by the point and manipulating the point alters the lesion contour.

In one example, the method further includes displaying an interventional instrument in a position relative to the image. In one example, the position of the interventional instrument is configured to be altered relative to the image. In one example, the method further includes displaying a location of a biopsy core overlying the image.

BRIEF DESCRIPTION OF THE DRAWINGS

The disclosure will be readily understood by the following detailed description in conjunction with the accompanying drawings, wherein like reference numerals designate like structural elements, and in which:

FIG. 17 illustrates exemplary "hemi-gland" margin;

DETAILED DESCRIPTION

Figure 1:
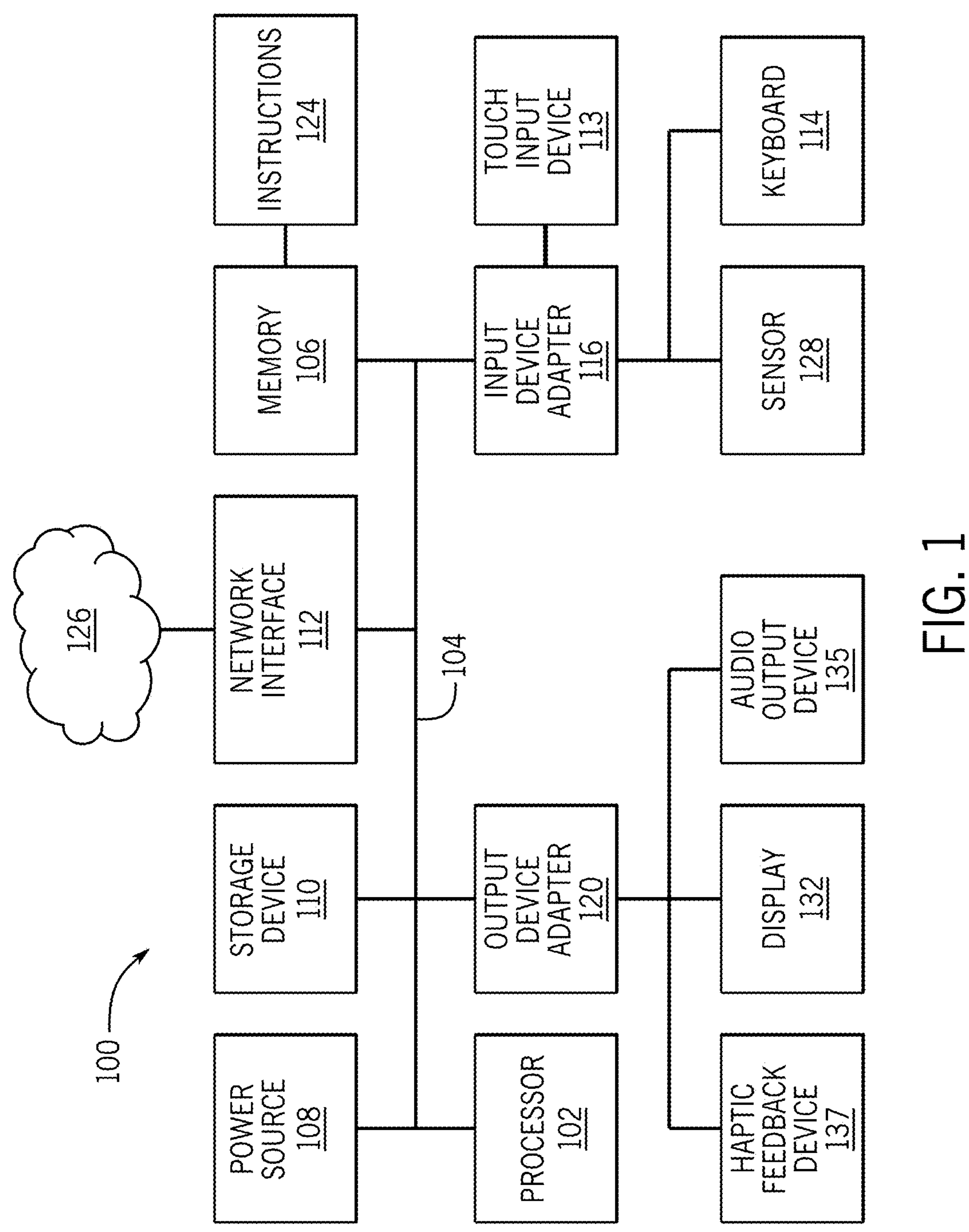
FIG. 1 illustrates a framework for a machine learning model that estimates the likelihood of a clinically significant cancer.

Reference will now be made in detail to representative embodiments illustrated in the accompanying drawings. It should be understood that the following descriptions are not intended to limit the embodiments to one preferred embodiment. To the contrary, it is intended to cover alternatives, modifications, and equivalents as can be included within the spirit and scope of the described embodiments as defined by the appended claims.

The following disclosure relates generally to systems and methods for detecting and characterizing cancerous lesions. More particularly, the present disclosure relates to systems and methods of identifying and characterizing cancerous lesions using machine learning algorithms.

Conventional MRI and biopsy techniques used for detecting cancerous lesions provide general cancer lesion localization, indicating the existence of a cancerous lesion. After detecting cancer, radiation therapy, chemotherapy, hormone therapy, surgery, ablative therapy, and/or other methods of cancer treatment are applied. This treatment approach can lead to unnecessarily excessive exposure of radiation or chemotherapy to the tissue or organ with the cancerous lesion or the unnecessary removal of healthy tissue surrounding the cancerous cells.

While the methods and systems described herein for detecting and mapping cancer in a patient can be applied to many or all forms of cancer, one example is the detection and mapping of prostate cancer. Traditional methods can lead to an overexposure of radiation or ablative therapy to the prostate or the removal of healthy prostate tissue, which can negatively impact urinary, sexual, and/or bowel functions, inducing a lower quality of life for the affected patient.

The methods and systems for detecting and mapping cancer described herein can more precisely identify cancerous lesions to minimize the negative effects on surrounding healthy tissues, including methods for increasing confidence in a mapped threshold of a lesion. In one example of the methods described herein, a machine learning algorithm can receive MRI and biopsy data, including biopsy pathology labels, as inputs to determine lesion thresholds and the likelihood of cancer encapsulation, with associated encapsulation confidence scores, to minimize the risk of overexposure and over-resection during ablative, radiation, and/or surgical interventions. The machine learning algorithms described herein can be trained on large-population datasets to increase the accuracy of cancer mapping, confidence scores, and threshold boundaries. In at least one example, the algorithm can output an estimate of clinically significant cancer likelihood at each voxel of a three-dimensional image.

These lesion encapsulation boundaries and associated confidence scores can be visually presented to a physician to communicate important information used to determine optimal intervention strategies. These visual outputs can include cancer estimation maps (CEM) showing a heat map of the lesion location overlying a medical image of the patient's anatomy, and a three-dimensional cancer lesion contour (CLC) enclosing a region of elevated cancer likelihood. Mapping cancer, as described herein, a CEM can indicate a spatial likelihood of tumor presence while a CLC can indicate an estimated tumor extent. While examples of systems described herein include a CEM, the systems described herein can be applied to both CEM mapping and/or CLC generation. In addition, the systems described herein can visually output a plot or curve of encapsulation confidence vs. lesion size. These outputs can be altered by the physician as the physician sees fit during analysis when balancing the risk of removing or affecting healthy tissue vs. the risk of missing cancerous cells during treatment, as presented by the confidence score curve.

In at least one example described herein, the CEM can be used alone or in combination with other factors to assess the stage of cancer. In at least one example, the cancer is prostate cancer and the stage assessment includes an estimation of the likelihood and/or location of extraprostatic extension. In at least one example, the CEM can be used alone or in combination with other factors to assess the patient's suitability for a course of treatment.

In some examples, inputs from at least one, two, or more data elements, such as medical imaging including MRI imaging, X-ray and ultrasound imaging, other relevant medical imaging, tracked biopsy, biopsy pathology, biopsy core locations, fusion based biopsy data, biomarkers such as PSA, patient demographics such as age, genomic markers, and or other inputs can be utilized by a machine learning algorithm, which can output an estimate of clinically significant cancer at each voxel of a three-dimension image to create the CEM, CLC, and the encapsulation confidence score noted above. The estimate of clinically significant cancer can be used to identify and narrow treatment therapies (e.g., chemotherapy, radiation, surgery, etc.). In one example, the encapsulation confidence score represents the estimated likelihood that a lesion contour encompasses all csPCa The machine learning algorithms of the present disclosure can be trained on large population datasets to hone individual CEMs for specific patients. Thresholding the CEM can be based on this population analysis. This training data set can be used as ground truth for training the algorithm and can include some or all of the inputs noted above for a large population, as well as other inputs specific to certain types of cancer or other inputs including post-care data and outcomes. The algorithm can then differentiate the probability of cancer at any point within a certain anatomy of the patient. In addition, a smaller sub-dataset using surgery data can be used a "tuning" data set for the algorithm, enabling an estimation of tumor encapsulation probability for a specific CLC and patient.

While the described methods and systems can apply to many or all cancerous lesions, prostate cancer is described herein as an example for purposes of explanation and illustration. The machine learning algorithms described herein can include additional inputs beyond those noted above, for example inputs specific to certain types of cancers. In the case of prostate cancer, the inputs noted above can be combined with additional data inputs, such as prostate-specific antigen (PSA) levels, and processed by a machine learning algorithm to provide a specific area within the prostate that is affected, leading to a more effective treatment and reducing the impact of urinary, sexual, and/or bowel compilations.

In another example, inputs from one, two, or more data elements are analyzed, producing an output including a cancer estimation map (CEM), otherwise referred to as a cancer probability map (CPM). It should be understood within the context of this disclosure the words cancer estimation map (CEM) and cancer probability map (CPM) are used interchangeably and define the likelihood of clinically significant prostate cancer at each voxel of a 3-dimensional image.

In one example, the method further includes a display of metadata and predictive statistics derived from the cancer estimation map, encapsulation confidence score, or tertiary statistical models. In one example, the metadata includes the encapsulation confidence score, which represents the probability of all clinically significant cancer being contained within a specified lesion contour. In one example, the metadata includes the lesion contour volume. In one example, the predictive statistics include an estimate of the tumor volume. In one example, the predictive statistics include an estimation of the cancer stage. In one example, the predictive statistics include an estimated likelihood of extracapsular extension, with or without a probable location of extracapsular extension. In one example, the predictive statistics include an estimation of the patient's suitability for a course of treatment such as ablative therapy, radiation, radical prostatectomy, or active surveillance. In one example, the predictive statistics include the estimated outcome of a course of treatment such as the need for additional treatment, the probability of biochemical recurrence or metastasis, the probability of treatment-related side effects, or the probability of death.

In another example, the output of the machine learning algorithm is further processed, or a second machine learning algorithm is used, to convey additional metadata or information beyond the visual representation of the CEM, CLC, and ECS. For example, a patient's automatically estimated suitability for a particular treatment (radiation, surgery, ablative therapy . . . etc.) can be displayed, with or without an estimate of the success probability for that treatment. In another example, the estimated cancer stage can be displayed, with or without localization and quantification of potential sites for invasive cancer on or beyond the organ of interest. Such information can be used to further help identify and narrow treatment options (e.g., chemotherapy, radiation, surgery, etc.).

These and other embodiments are discussed below with reference to FIGS. 1-28. However, those skilled in the art will readily appreciate that the detailed description given herein with respect to these Figures is for explanatory purposes only and should not be construed as limiting. Furthermore, as used herein, a system, a method, an article, a component, a feature, or a sub-feature comprising at least one of a first option, a second option, or a third option should be understood as referring to a system, a method, an article, a component, a feature, or a sub-feature that can include one of each listed option (e.g., only one of the first option, only one of the second option, or only one of the third option), multiple of a single listed option (e.g., two or more of the first option), two options simultaneously (e.g., one of the first option and one of the second option), or combination thereof (e.g., two of the first option and one of the second option).

While the embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the instant disclosure covers all modifications, equivalents, and alternatives falling within the scope of the appended claims.

FIG. 1 shows a high-level block diagram of a computer system 100 that can be used to implement embodiments of the present disclosure. In various embodiments, the computer system 100 can comprise various sets and subsets of the components shown in FIG. 1. Thus, FIG. 1 shows a variety of components that can be included in various combinations and subsets based on the operations and functions performed by the system 100 in different embodiments. It is noted that, when described or recited herein, the use of the articles such as "a" or "an" is not considered to be limiting to only one, but instead is intended to mean one or more unless otherwise specifically noted herein.

The computer system 100 can comprise a central processing unit (CPU) or processor 102 connected via a bus 104 for electrical communication to a memory device 106, a power source 108, an electronic storage device 110, a network interface 112, an input device adapter 116, and an output device adapter 120. For example, one or more of these components can be connected to each other via a substrate (e.g., a printed circuit board or other substrate) supporting the bus 104 and other electrical connectors providing electrical communication between the components. The bus 104 can comprise a communication mechanism for communicating information between parts of the system 100.

The processor 102 can be a microprocessor or similar device configured to receive and execute a set of instructions 124 stored by the memory 106. The memory 106 can be referred to as main memory, such as random access memory (RAM) or another dynamic electronic storage device for storing information and instructions to be executed by the processor 102. The memory 106 can also be used for storing temporary variables or other intermediate information during execution of instructions executed by the processor 102. The power source 108 can comprise a power supply capable of providing power to the processor 102 and other components connected to the bus 104, such as a connection to an electrical utility grid or a battery system.

The storage device 110 can comprise read-only memory (ROM) or another type of static storage device coupled to the bus 104 for storing static or long-term (i.e., non-dynamic) information and instructions for the processor 102. For example, the storage device 110 can comprise a magnetic or optical disk (e.g., hard disk drive (HDD)), solid state memory (e.g., a solid state disk (SSD)), or a comparable device. The instructions 124 can comprise information for executing processes and methods using components of the system 100

The network interface 112 can comprise an adapter for connecting the system 100 to an external device via a wired or wireless connection. For example, the network interface 112 can provide a connection to a computer network such as a cellular network, the Internet, a local area network (LAN), a separate device capable of wireless communication with the network interface 112, other external devices or network locations, and combinations thereof. In one example embodiment, the network interface 112 is a wireless networking adapter configured to connect via WI-FI®, BLUETOOTH®, BLE, Bluetooth mesh, or a related wireless communications protocol to another device having interface capability using the same protocol. In some embodiments, a network device or set of network devices in the network 126 can be considered part of the system 100. In some cases, a network device can be considered connected to, but not a part of, the system 100.

The input device adapter 116 can be configured to provide the system 100 with connectivity to various input devices such as, for example, a touch input device 113 (e.g., display or display assembly), a keyboard 114 or other peripheral input device, one or more sensors 128, related devices, and combinations thereof. In some configurations, the input device adapter 116 can include the touch controller or similar interface controller described above. The sensors 128 can be used to detect physical phenomena in the vicinity of the computing system 100 (e.g., light, sound waves, electric fields, forces, vibrations, etc.) and convert those phenomena to electrical signals. The keyboard 114 or another input device (e.g., buttons or switches) can be used to provide user input such as input regarding the settings of the system 100.

The output device adapter 120 can be configured to provide the system 100 with the ability to output information to a user, such as by providing visual output using one or more displays 132, by providing audible output using one or more speakers 135, or providing haptic feedback sensed by touch via one or more haptic feedback devices 137. Other output devices can also be used. The processor 102 can be configured to control the output device adapter 120 to provide information to a user via the output devices connected to the adapter 120.

Any of the features, components, and/or parts, including the arrangements and configurations thereof shown in FIG. 1 can be included, either alone or in any combination, in any of the other examples of devices, features, components, and parts shown in the other figures. For example, the computing system 100 can be used to run the algorithms described herein and display the visual representations described herein and shown in other figures. Likewise, any of the features, components, and/or parts, including the arrangements and configurations thereof shown in the other figures can be included, either alone or in any combination, in the example of the devices, features, components, and parts shown in FIG. 1.

Figure 2:
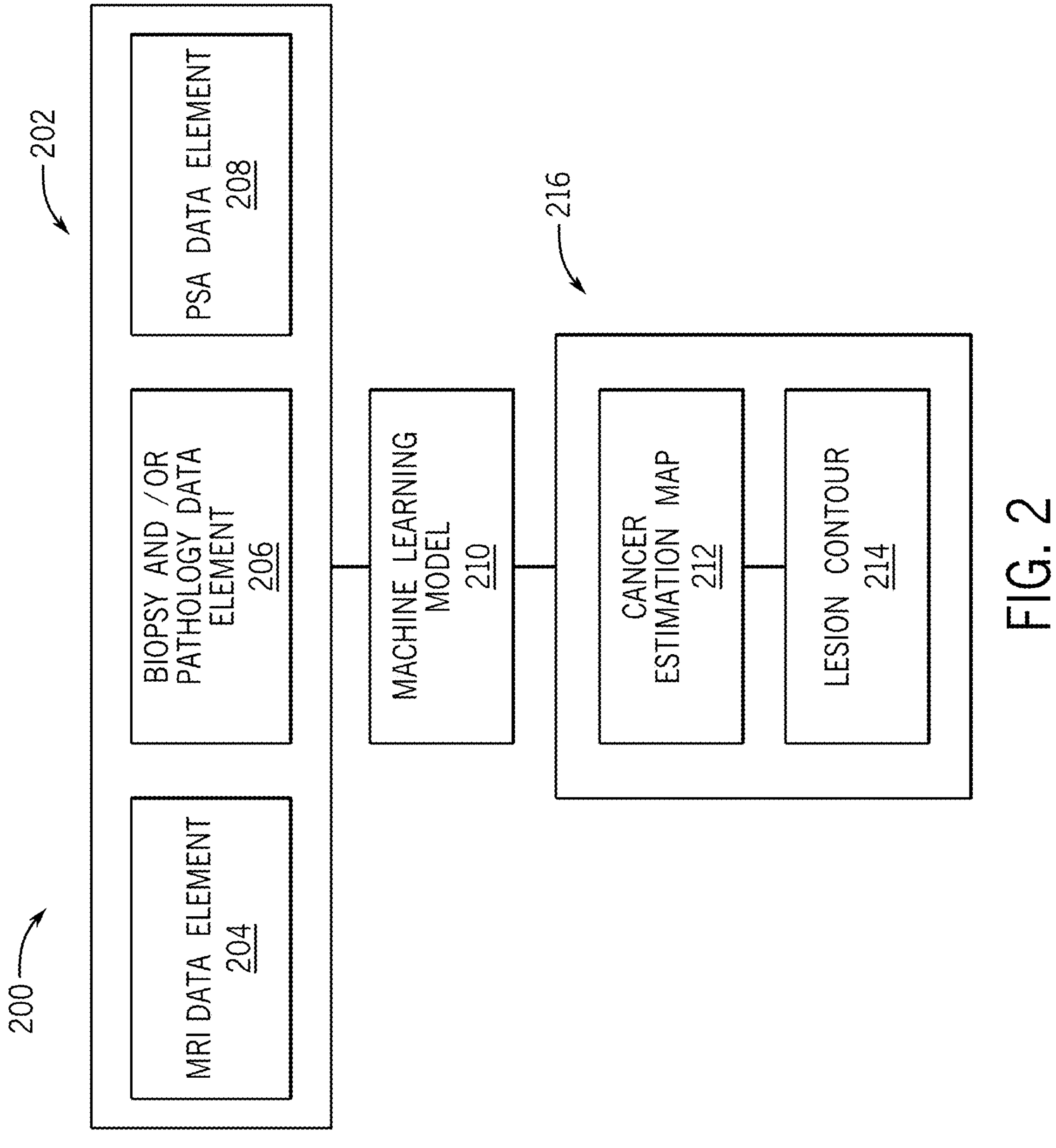
FIG. 2 illustrates exemplary inputs and outputs of a machine learning model that estimates the likelihood of a clinically significant cancer.

FIG. 2 illustrates an exemplary data flow diagram 200 of a machine learning model estimating the likelihood of clinically significant cancer. As an example, the systems described herein are described with reference to prostate cancer. However, the systems and methods described herein can be applied to other types of cancer as well. In at least one example, a software program can utilize at least one, two, or many data elements as an input 202 including an MRI data element 204, a biopsy pathology data element 206, a prostate specific antigen (PSA) data element 208, and/or other data elements for determining cancer probability. The detection of prostate cancer, and specifically the use of PSA as an input to systems described herein, are exemplary only and not meant to be limiting. Rather, as noted above, the systems and methods described herein can be applied to other types of cancers with other types of antigens, imaging modalities, genetic information, demographic data, or biomarkers indicative of other types of cancer used as inputs to the system. In one example, the input 202 can exclude the PSA data element 208.

In at least one example, the data elements 204, 206, 208 can serve as the input 202 to the machine learning model 210. The machine learning model can a single model, multiple models operating in series or in parallel, and/or one or more models with the addition of post-processing analyses. In one example, the machine learning model 210 can then estimate the likelihood of clinically significant cancer. In one example, clinically significant cancer can be defined as Gleason grade group 2 or higher disease in the case of prostate cancer. In at least one example, the machine learning model 210 can subsequently provide an output 216 including an estimate of clinically significant cancer likelihood at each voxel of a 3D image defined herein as a cancer estimation map (CEM) 212. The final output can be a lesion contour 214. The lesion contour can be a 3D surface generated thresholding of cancer probability. The output can include additional data related to or derived from the machine learning model such as the estimated probability of tumor encapsulation, an estimate of tumor staging, an estimate of the patient's suitability for a particular therapy (surgery, radiation, ablative therapy . . . etc.), a segmentation of the tumor, and/or a segmentation of anatomical structures (the prostate, urethra, bladder, seminal vesicles, prostatic zones, vas deferens, rectum, pelvic bone . . . etc.).

Any of the features, components, and/or parts, including the arrangements and configurations thereof shown in FIG. 2 can be included, either alone or in any combination, in any of the other examples of devices, features, components, and parts shown in the other figures. Likewise, any of the features, components, and/or parts, including the arrangements and configurations thereof shown in the other figures can be included, either alone or in any combination, in the example of the devices, features, components, and parts shown in FIG. 2.

Figure 3:
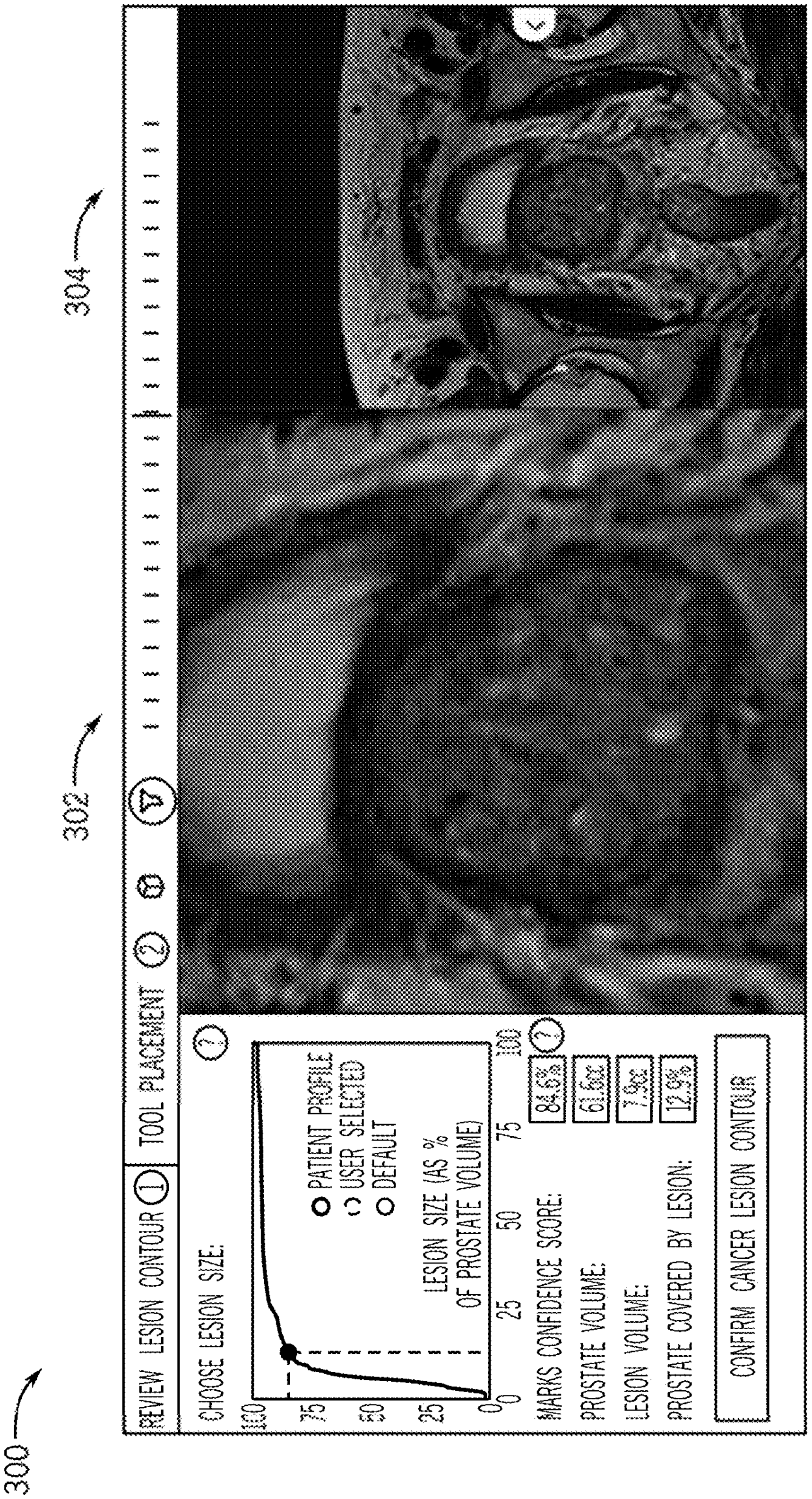
FIG. 3 illustrates an MRI data element.

FIGS. 3-28 illustrate examples of the output 216 shown in FIG. 2 of a machine learning algorithm, as well as additional data related to or derived from the machine learning model. The outputs shown in FIGS. 3-28 can be visually represented on a display screen to a physician or other user when a software program executing the machine learning algorithm or the output of the machine learning algorithm is run by a computing device. In one example, as shown in FIG. 3, an input 302 can include a magnetic resonance image (MRI) 300 of a patient utilized as an MRI data element 304 can be displayed. The MRI data element 204 can contain information related to the MRI coordinate space and can be one of the inputs 202 into the machine learning model 210, as discussed in FIG. 2. The MRI data element 204 can be one or more MRI sequences (T2-weighted, diffusion-weighted, perfusion-weighted, etc.) derived from the same patient.

Figure 4A:
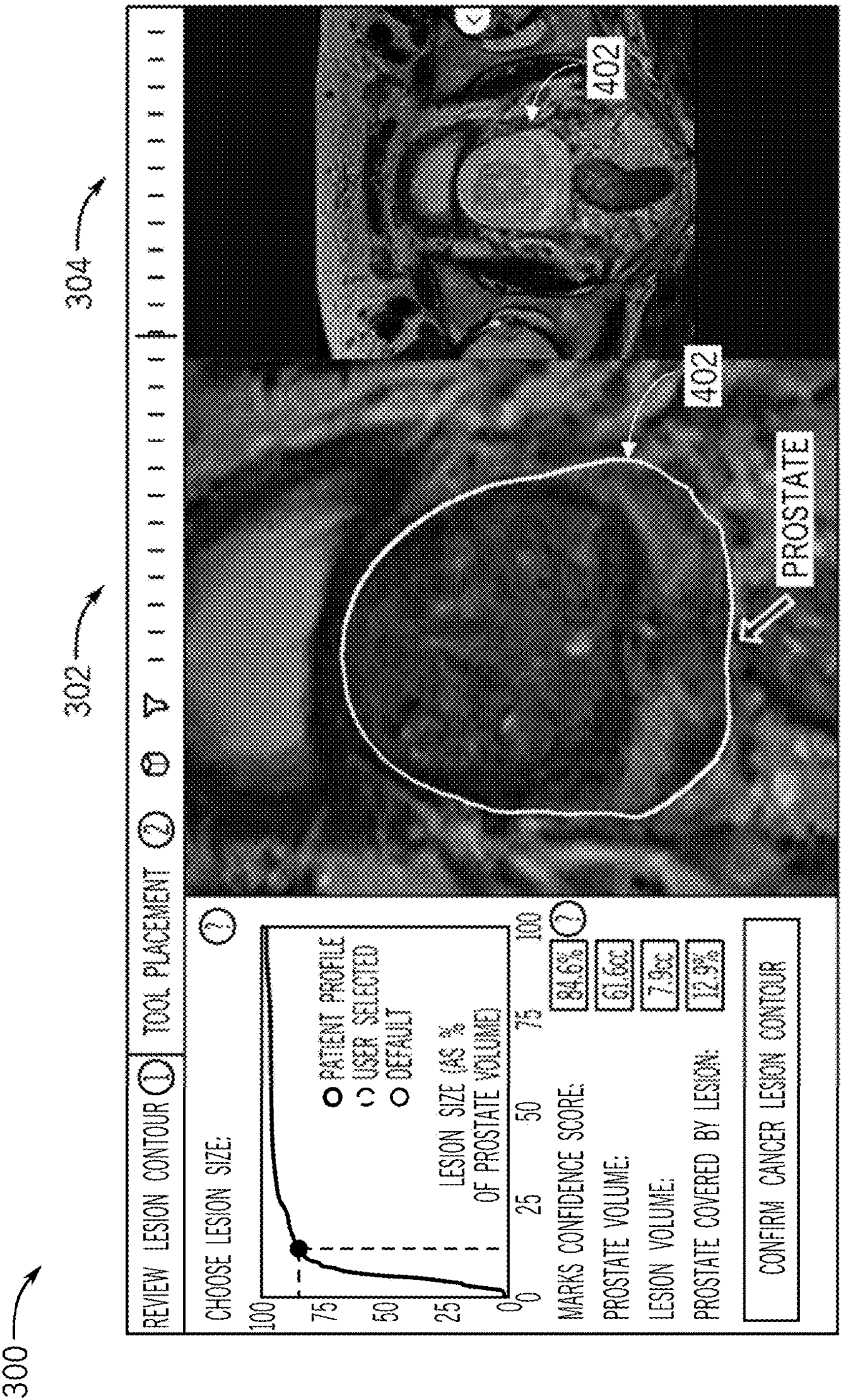
FIGS. 4A-4B illustrate additional data elements including a prostate segmentation and a region of interest (ROI) as outputs of a machine learning model.
Figure 4B:
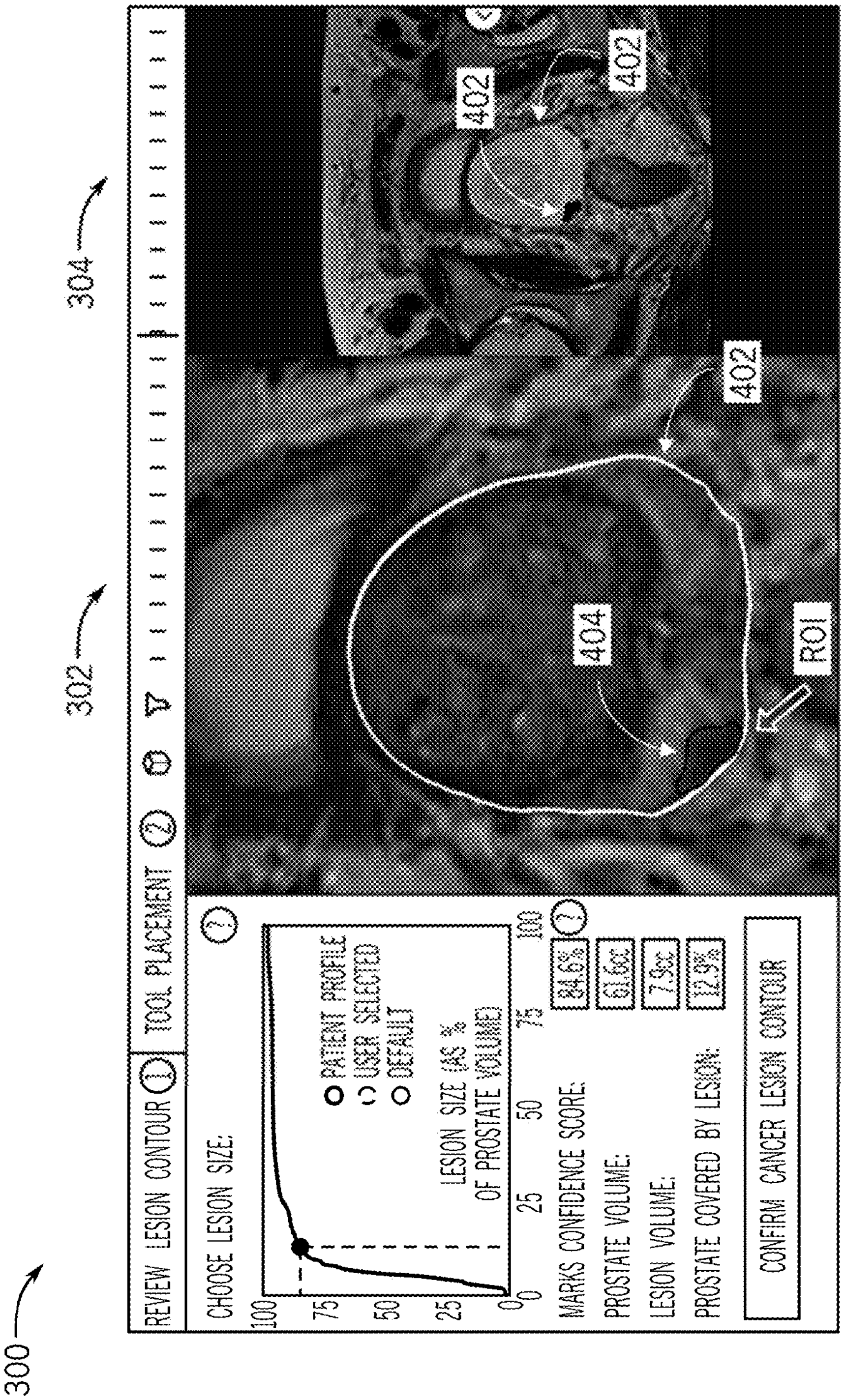

FIG. 4A illustrates the exemplary prostate MRI 300, as discussed previously in FIG. 3, including an exemplary prostate segmentation 402 identified by the machine learning model 210. FIG. 4B illustrates the exemplary prostate MRI 300 of a patient including the exemplary prostate segmentation 402 and a region of interest (ROI) 404 identified by the machine learning model 210 as an output.

Figure 5A:
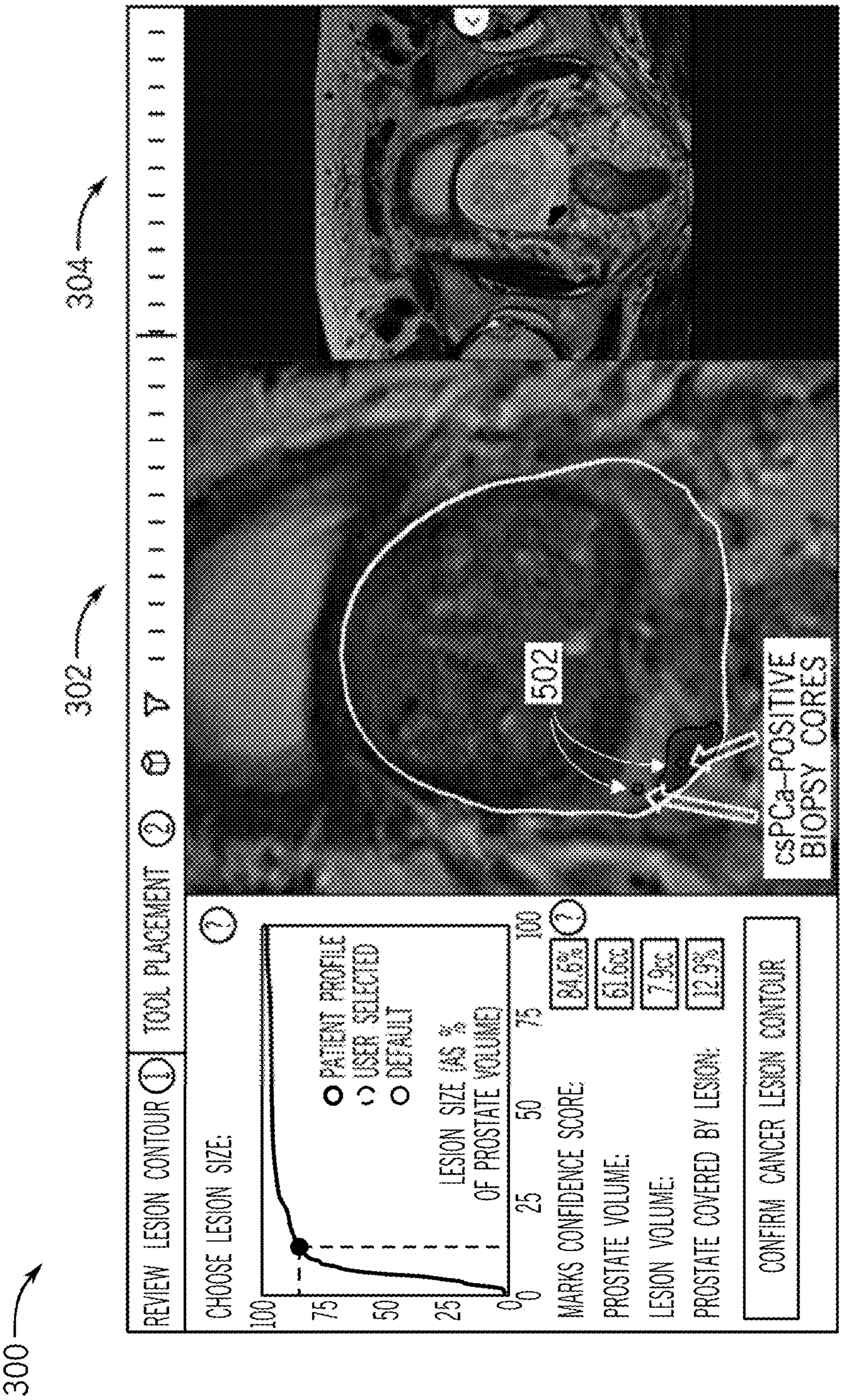
FIGS. 5A-5B illustrate csPCa-Positive and csPCa-Negative biopsy core data elements.
Figure 5B:
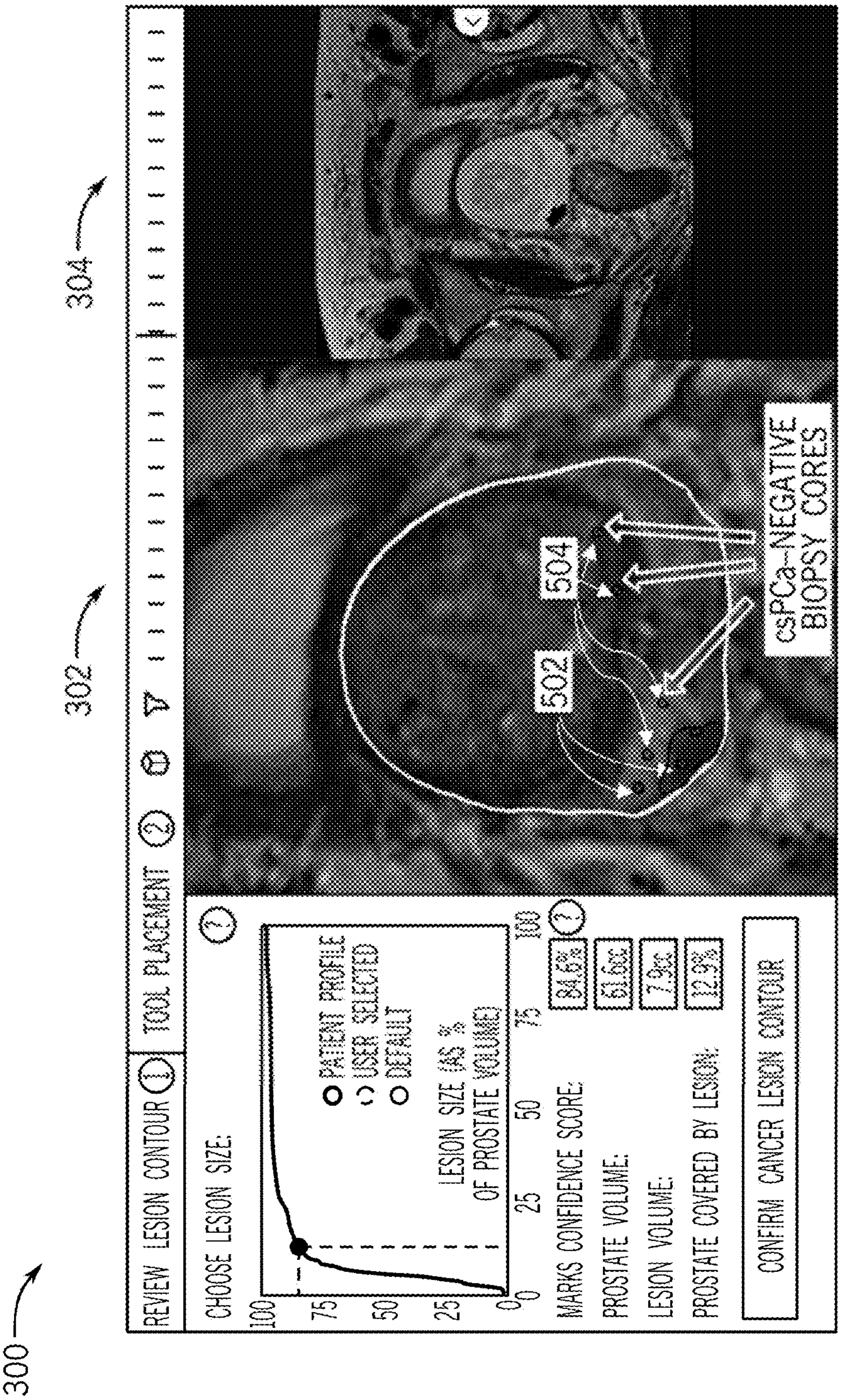

FIG. 5A illustrates csPCa-Positive biopsy core(s) 502 derived from a biopsy system, for example, a biopsy system that registers or fuses the biopsy locations with the MRI data elements. For example, a patient can receive a biopsy from a biopsy system with identified csPCa-Positive cores and the core location(s) on the prostate gland can be digitally transcribed onto the MRI image relative to the prostate segment 402, as discussed in FIG. 4A. Similarly, FIG. 5B illustrates csPCa-Negative biopsy core(s) 504 identified with a biopsy system capable of tracking the core location(s) within the prostate gland. The location data of the csPCa-Negative biopsy core(s) 504 is received as an input to the machine learning model 210 and represented in a color differing from the csPCa-Positive biopsy core(s) 502. For example, the csPCa-Positive biopsy core(s) 502 can be represented by the color red, while the csPCa-Negative biopsy core(s) 504 can be represented by the color blue, creating a visually distinguished difference between positive and negative biopsy cores 502, 504. Additional cores that fit into other categories can be represented by one or more tertiary colors. For example, biopsy core(s) containing clinically insignificant cancer can be represented by the color orange.

Figure 6:
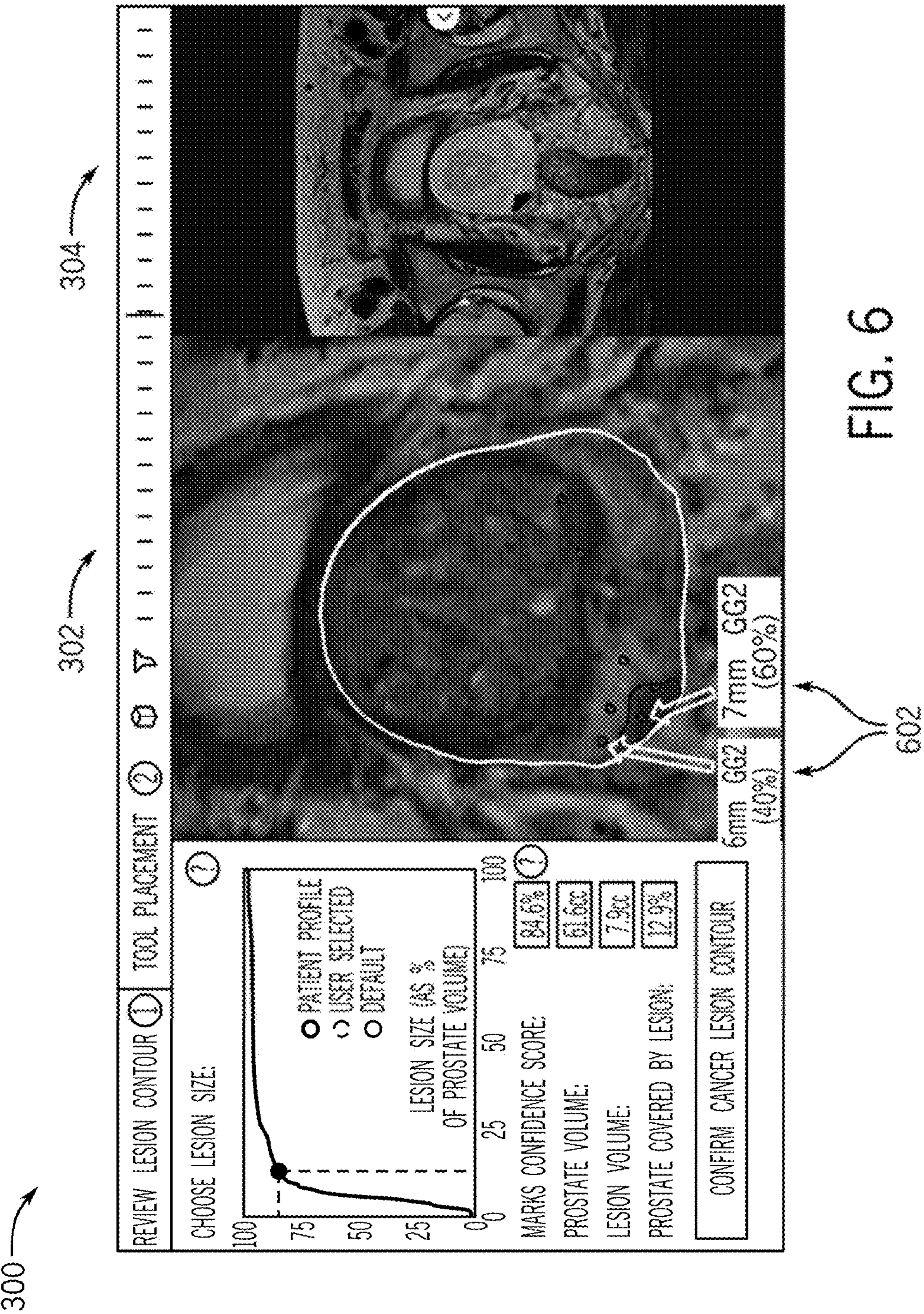
FIG. 6 illustrates biopsy data elements from biopsy locations merged with MRI data elements.

As illustrated in FIG. 6, each biopsy core 502, 504 is labeled with one, two, or many attributes 602, such as a Gleason score, cancer percentage, cancer length, and core length as determined and documented in a pathology report by a pathologist or pathology analysis algorithm.

Figure 7:
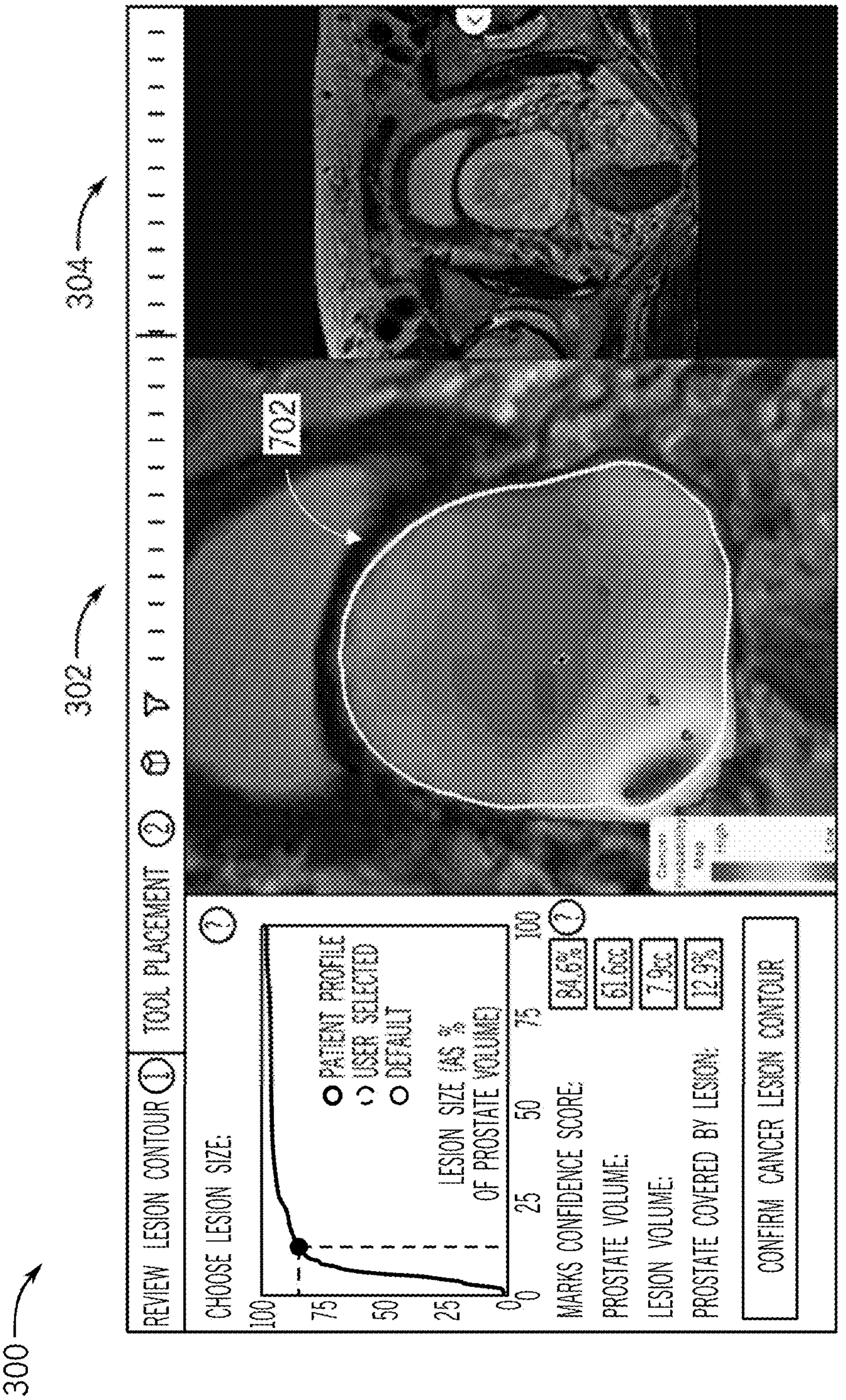
FIG. 7 illustrates a cancer estimation map (CEM)

FIG. 7 provides a visual representation of a Cancer Estimation Map (CEM) 702 as one exemplary output of the machine learning model 210. The CEM 702 identifies the probability of cancerous locations based on a color gradient (e.g., heat map) which provides a visual representation of the probability of cancerous tissue at specific location relative to the prostate segment 402. For example, as discussed in FIG. 2, the machine learning model 201 can receive one, two, or many inputs (e.g., tracked biopsy, biopsy pathology, and prostate specific antigen (PSA)) and estimate, as an output 216, the prostate segmentation 402, the region of interest 404, and/or the cancer probability map 702. The outputs 402, 404, 702 increase the accuracy and efficacy of prostate cancer treatment and/or reduce the amount of prostate tissue removed or damaged when compared to conventional prostate treatment methods.

Figure 8:
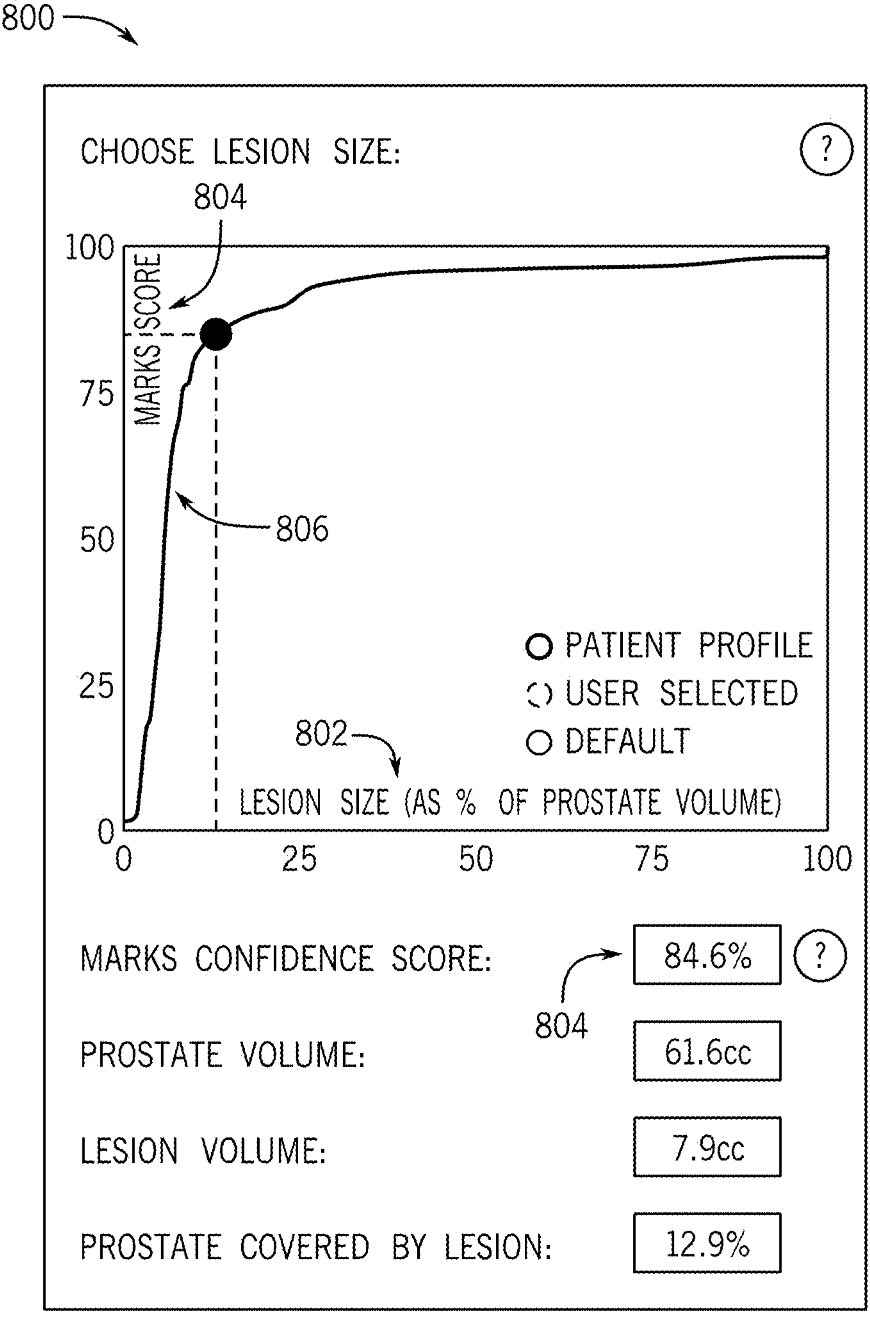
FIG. 8 illustrates a graphical user interface of a patient-specific chart.

The clinician is also presented with a patient-specific chart 800 representing the encapsulation confidence curve 806, otherwise referred to as a Marks confidence curve, as illustrated in FIG. 8. The x-axis 802 of the patient-specific chart 800 represents the percent of prostate voxels encapsulated by iterative thresholding of the CEM 702. The y-axis 804 of the patient-specific chart 800 represents the encapsulation confidence score, the confidence that all cancerous cells of the lesion will be encapsulated using each CEM threshold, with a range from zero to one hundred represented as a percentage. The encapsulation confidence score is based on a lookup table correlating the probability of csPCa encapsulation to CEM thresholds. The lookup table provides the clinician with data derived from retrospective studies of whole-mount pathology data.

Figure 9A:
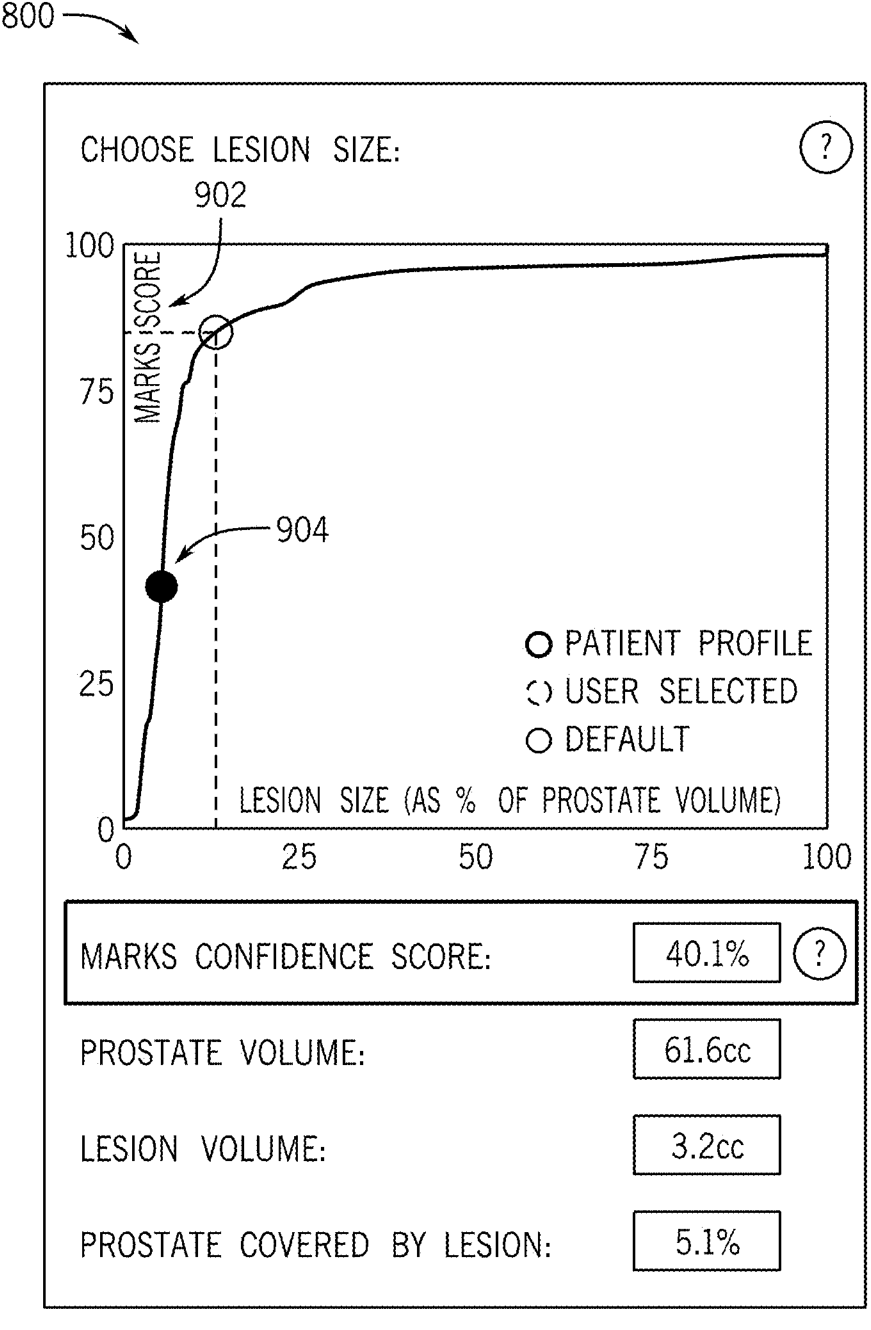
FIG. 9A-10B illustrate a lesion with a CEM and various lesion contours selected from various points on an encapsulation confidence score vs. lesion size curve.

As illustrated in FIG. 9A, the machine learning model 210 generates a default point 902 within the patient-specific chart 800. A default lesion contour is selected that maximizes the encapsulation confidence score 804, represented on the y-axis, while minimizing the lesion size 802, represented on the x-axis.

Figure 9B:
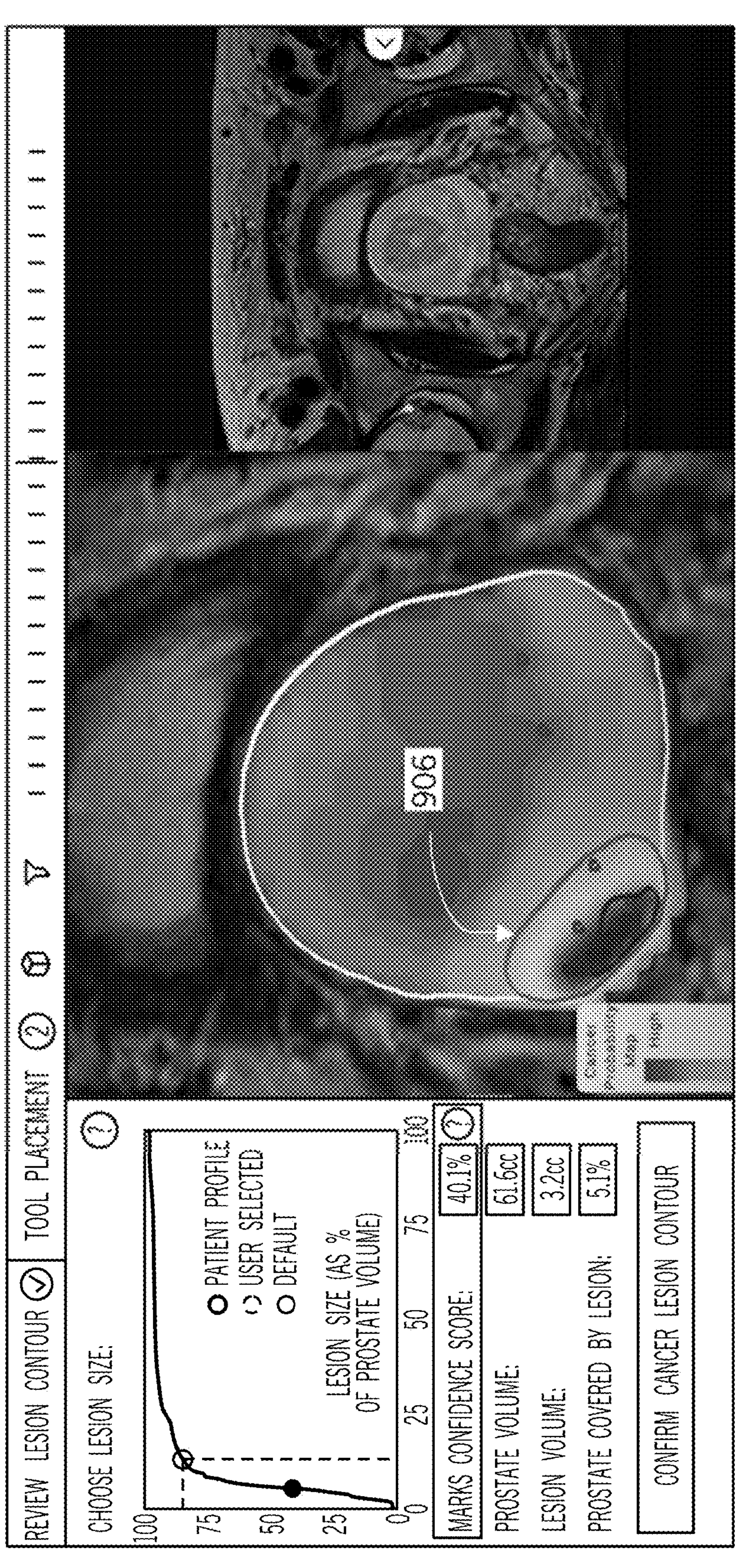

The lesion contour, shown in FIG. 9B, is generated after a point on the patient-specific chart is selected. For example, a user-selected point 904 on the patient-specific chart 800 selects a smaller lesion size 802 (shown in FIG. 8), represented on the x-axis, reducing the encapsulation confidence score 804 (also shown in FIG. 8), represented on the y-axis. The user-selected point 904 results in a lower encapsulation confidence than the default point 902. The resulting lesion contour size as indicated by the lesion contour 906, illustrated in FIG. 9B, which is overlaid on the CEM 702 creating a visual representation of the selected lesion contour size relative to the CEM 702, allowing a clinician to effectively "tune" the lesion contour size represented by the lesion contour 906, increasing the likelihood of treatment success or decreasing the volume of treatment.

Figure 10A:
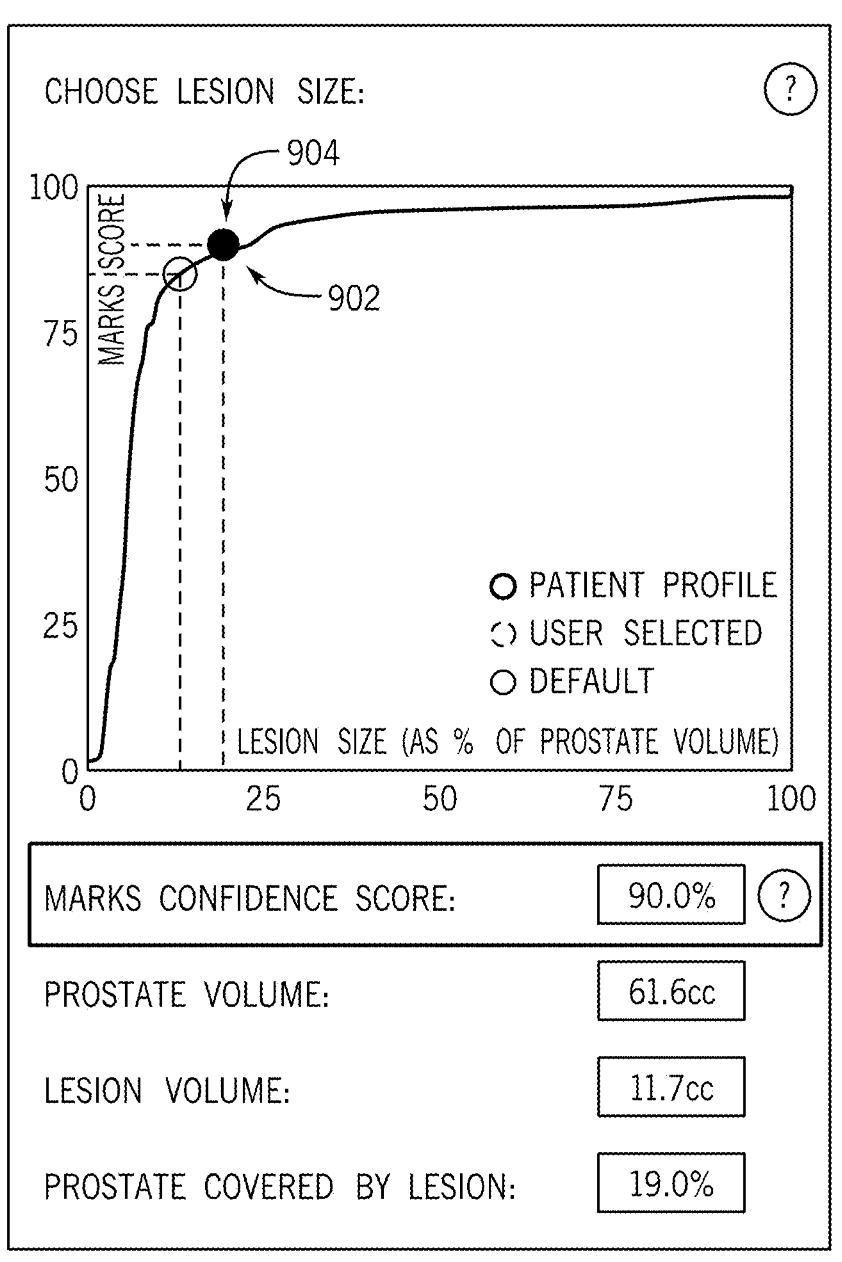
Figure 10B:
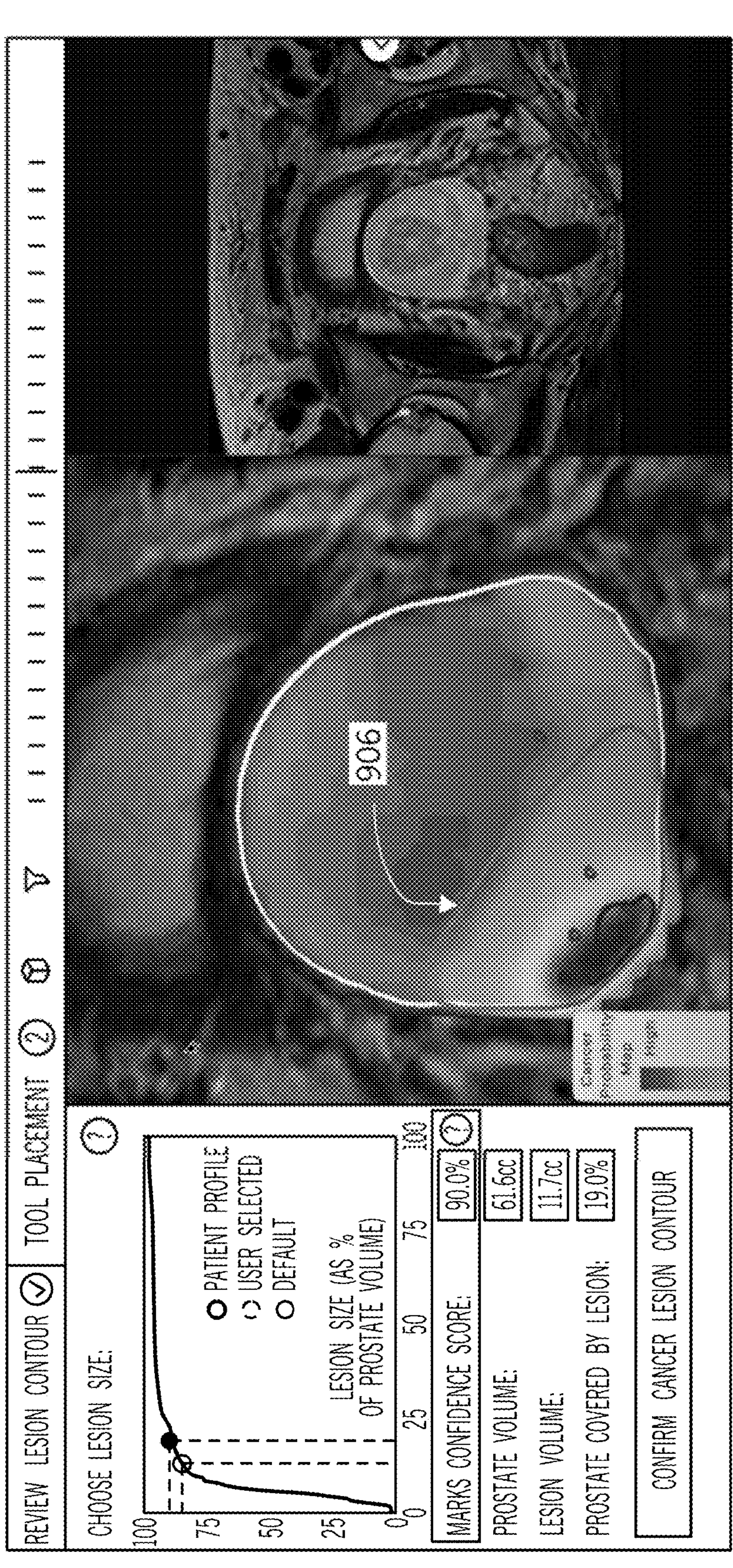

Similarly, FIGS. 10A-10B show the user-selected point 904 with an encapsulation confidence score 804 greater than the default point 902, increasing the lesion contour size on the X-axis, as represented by the lesion contour 906 on the CEM 702 above the default point 902 shown on the curve.

Users are free to adjust the lesion contour 906 representing the lesion contour size in the CEM 702 by selecting ant point on the encapsulation confidence curve 806. The encapsulation confidence curve 806 facilitates a balance between the likelihood of csPCa encapsulation against the lesion contour size. For example, as shown in FIGS. 9A-9B, a user can scale down the lesion contour size by selecting a lower CEM 702 threshold, subsequently updating the encapsulation confidence score 804. Conversely, as shown in FIGS. 10A-10B, a user can scale up the lesion contour size 96 by selecting to increase the encapsulation confidence score 804. The lesion contour size a user selects can depend on patient anatomy, physician expertise, the type of intervention being planned, and other factors.

Figure 11:
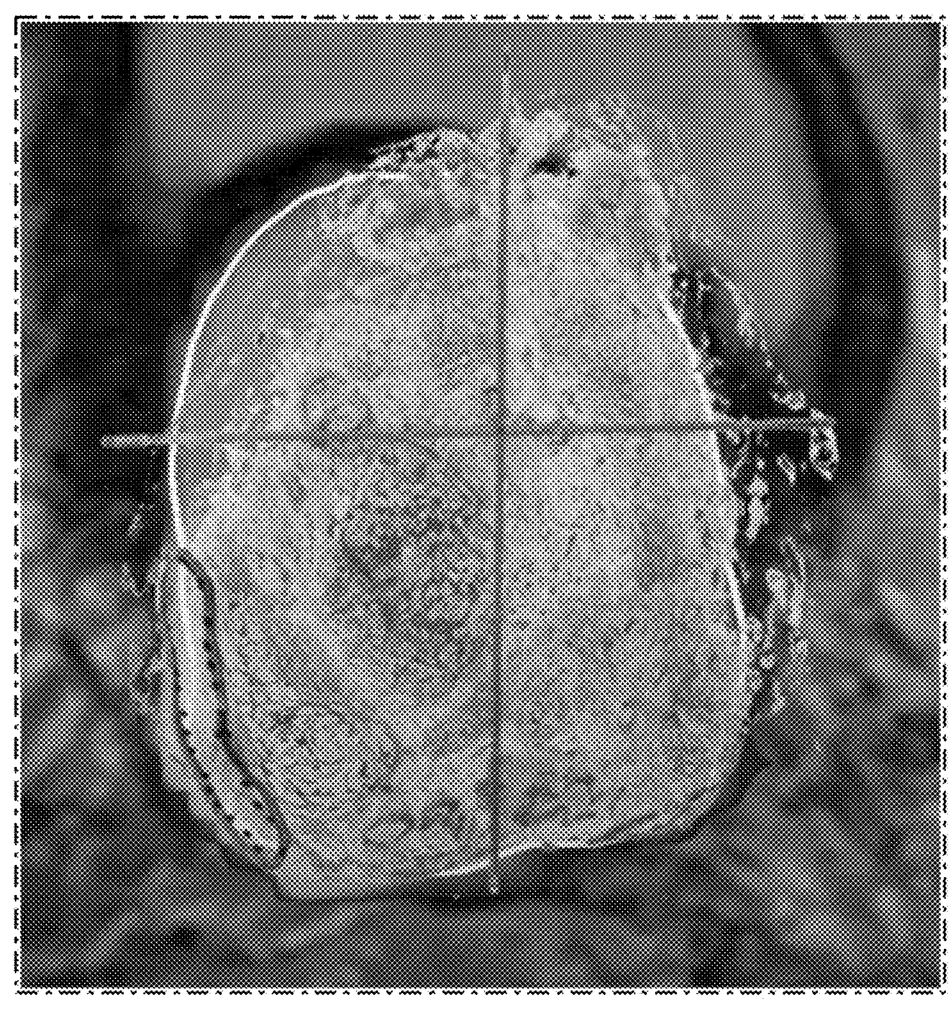
FIG. 11 illustrates 3D-reconstructed pathology regions.

As shown in FIG. 11, the cancer probability map 702 and lesion contours are evaluated using whole-mount pathology. The MRI registered and 3D-reconstructed pathology tumor regions are used to define ground truth csPCa, enabling precise and objective assessment of key software features, such as the encapsulation confidence curve 806.

Figure 12:
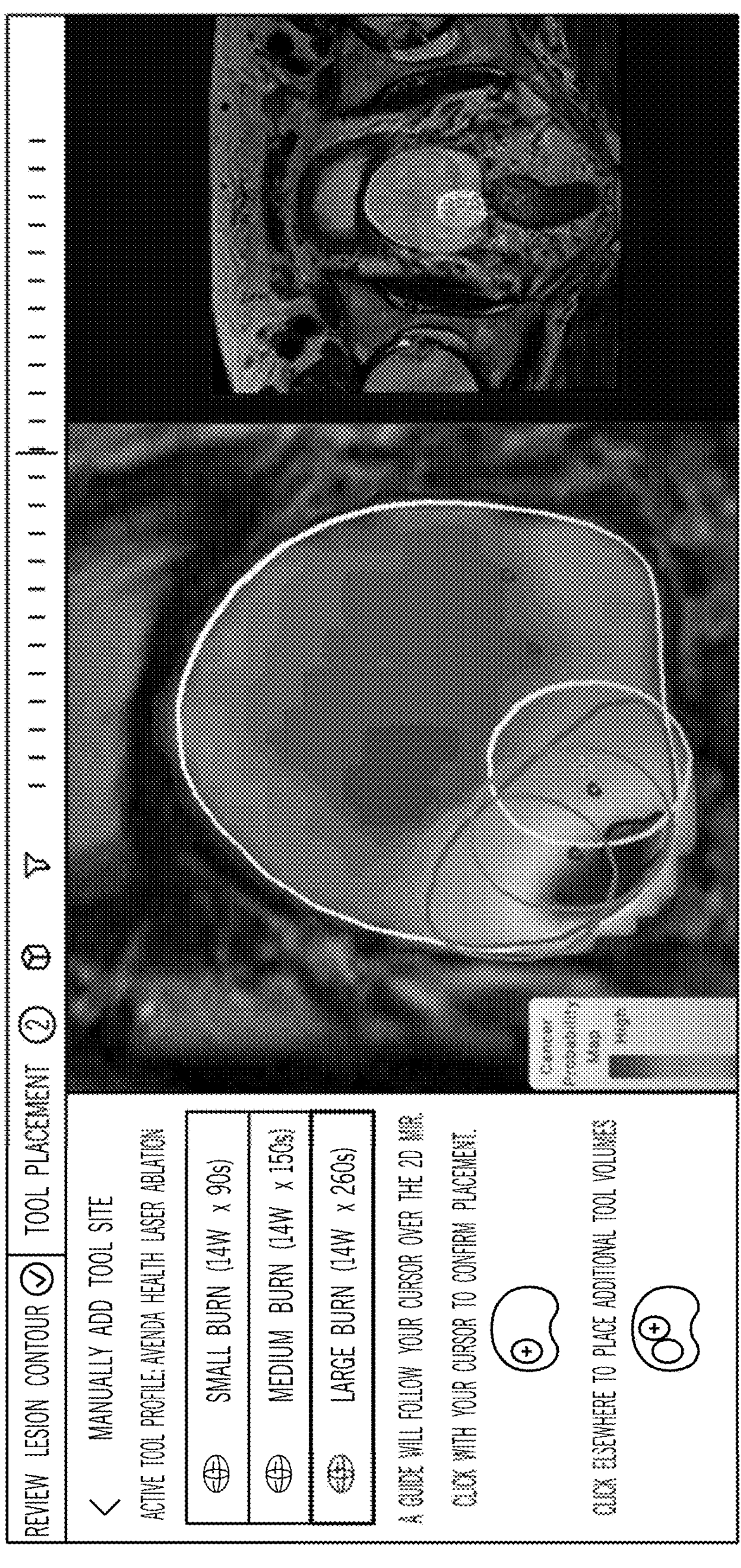
FIG. 12 illustrates an interventional tool selection.
Figure 13:
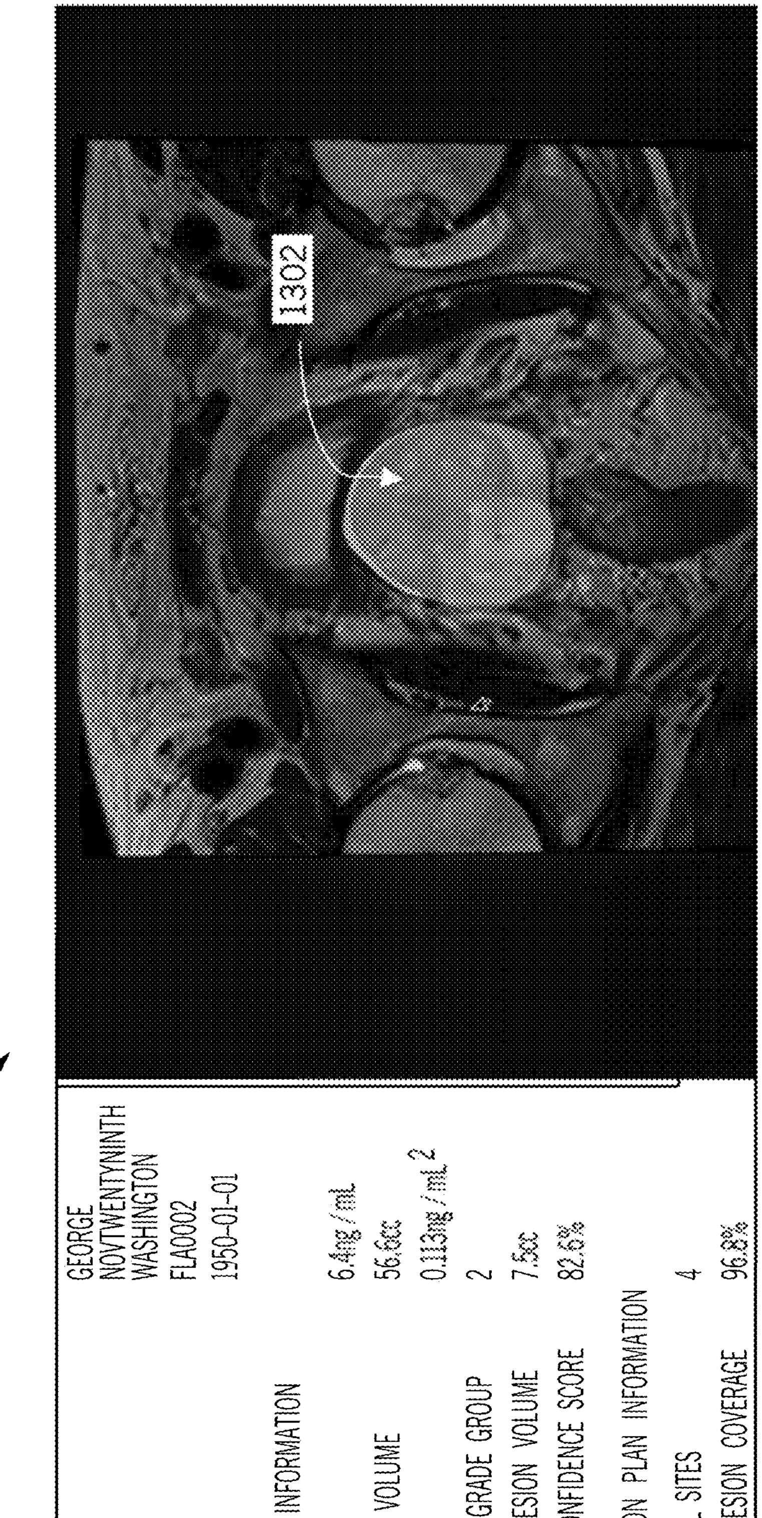
FIGS. 13-16B illustrate placement of an interventional tool in a three-dimensional representation of a prostate segmentation.
Figure 14:
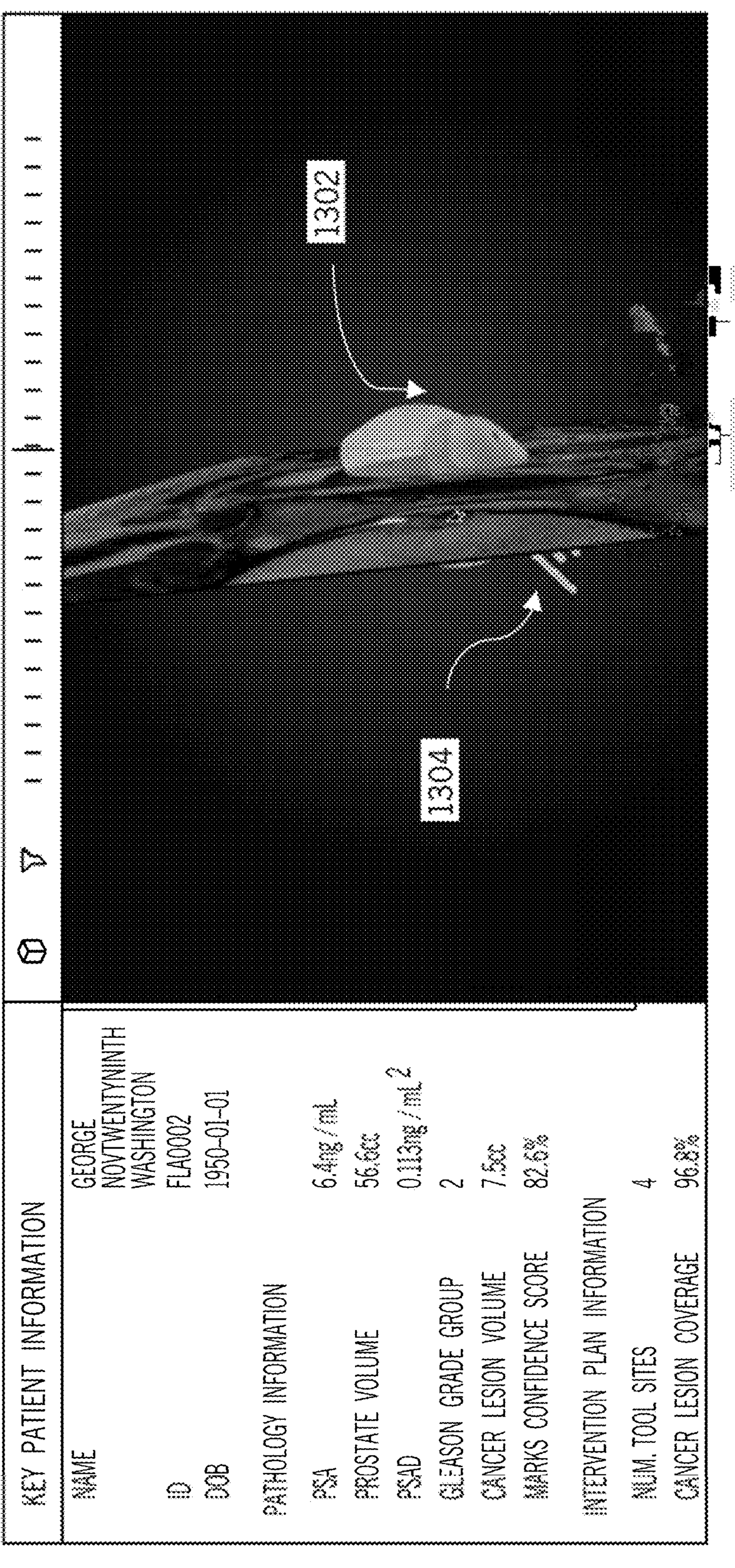
Figure 15:
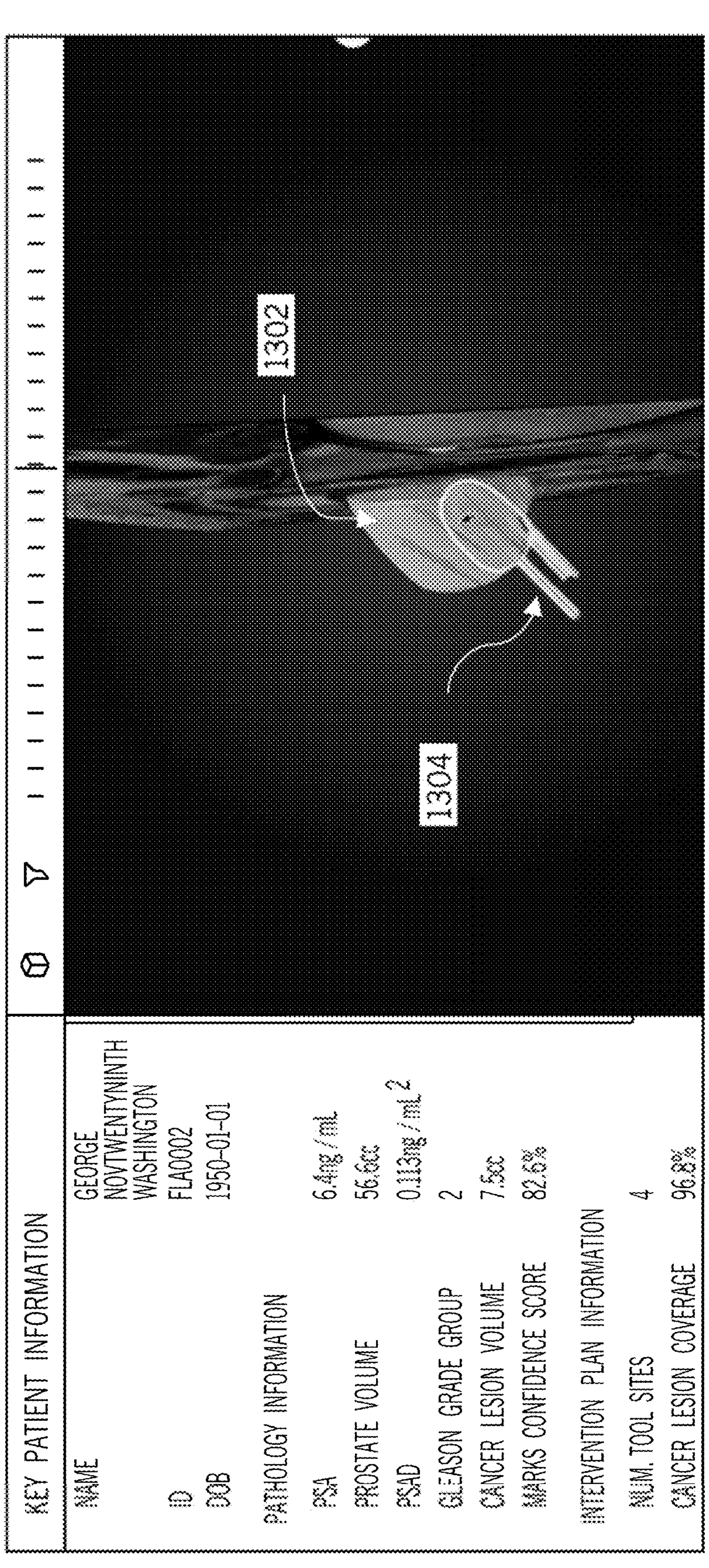

As illustrated in FIG. 12, once the cancer lesion contour size is confirmed, a user can place virtual interventional instruments with customizable dimensions. In one example, the instruments might represent interstitial catheters and the intervention might be thermal ablation of cancerous tissue. A user can select a tool applicable to a desired ablation size. For example, if a smaller cancer lesion contour size is identified, a smaller ablation size would be applicable. In the event a larger cancer lesion contour size is identified, a larger ablation size would be applicable. The ablation size location and orientation is user-selectable, and placement of interventional instruments is customizable with a user able to select manual or semi-automatic placement of the interventional instrument.

As shown in FIGS. 13-16B, a user can review the prostate segmentation 1302. In another example, a user can review the prostate segmentation 1302, cancer lesion contour 1305, and interventional instruments 1304. The interventional instrument 1304 location and quantity is identified and digitally represented to the user. In one example, the interventional instrument 1304 represents a probe for inducing tissue ablation, and the ablation volume associated with each probe is displayed relative to the image. In one example, the position of the interventional instrument 1304 and/or the ablation volume is compared to the position of other anatomy. In one example, the configuration of the interventional instrument 1304 and other anatomy may be identified as a potential cause safety for or efficacy concerns.

Figure 16A:
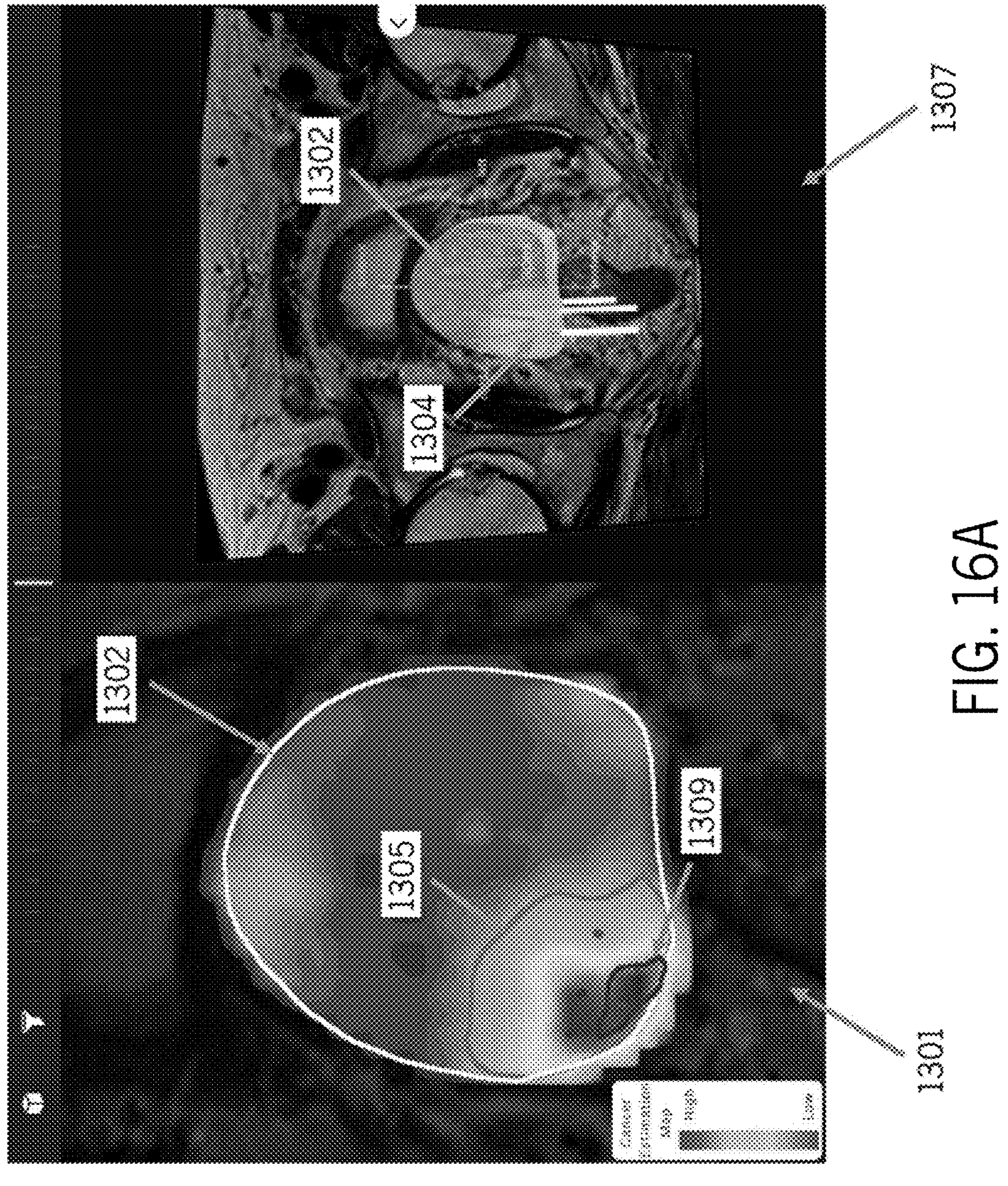
Figure 16B:
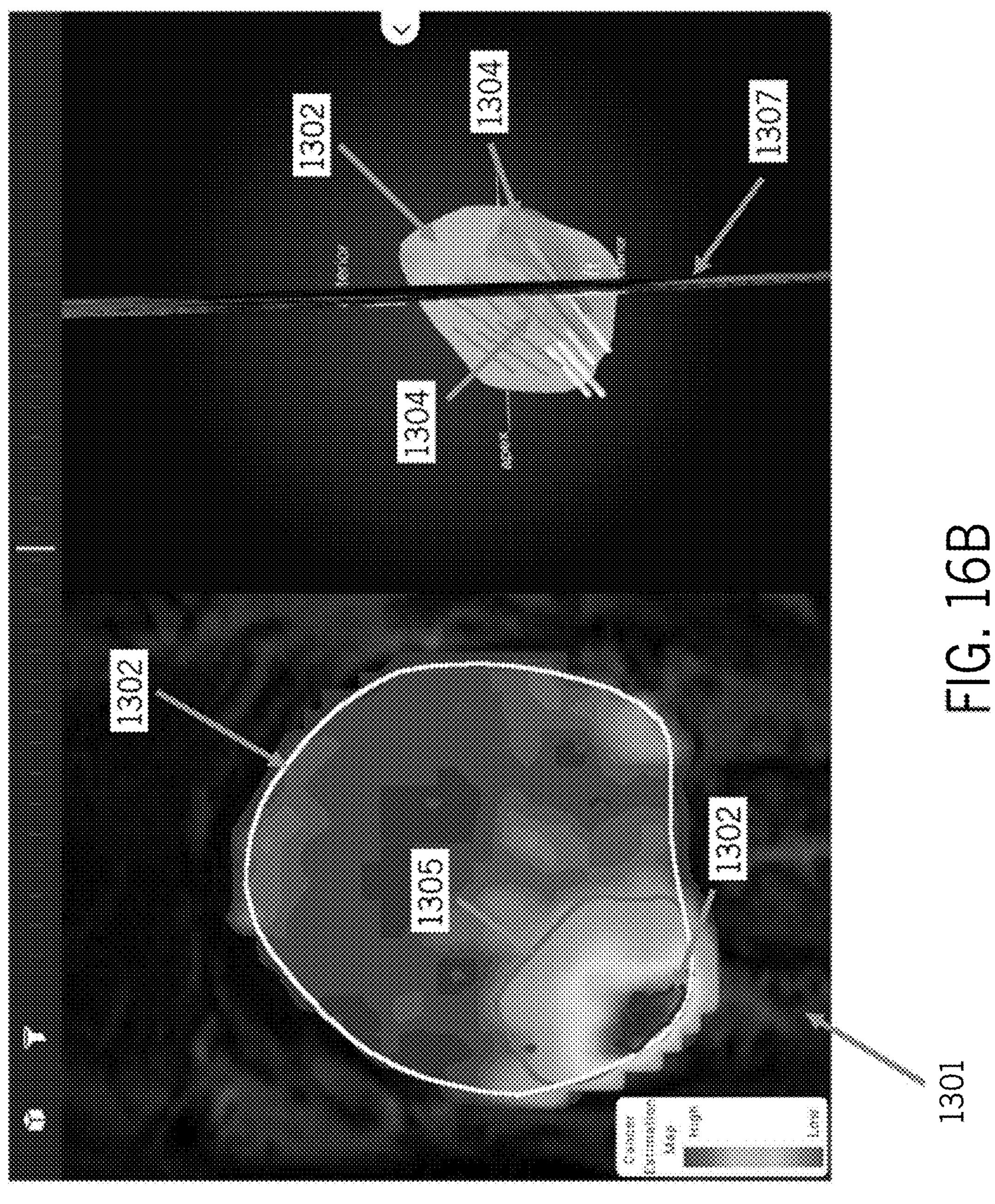

FIGS. 16A and 16B, in particular, show a CEM 1301 and a corresponding medical image 1307 showing a prostate segmentation 1302 and virtual interventional instruments 1304. FIG. 16A shows a plan view of the medical image 1307 and FIG. 16B shows a side view thereof to illustrate the three-dimensional information and nature of the segmentation 1302 and interventional instruments 1304 displayed. The medical image 1307 and the CEM 1301 can be shown side-by side to give visual context to the practitioner. The prostate segmentation 1302 can be represented in a three-dimensional space and the interventional instruments 1304 can be placed within the virtual three-dimensional space of the segmentation 1302. The position of the interventional instruments 1304 superimposed over or within the three-dimensional segmentation 1302 can correspond to recommended positions of actual instruments used during intervention. The CEM 1301 can include a segmentation 1302, lesion contour 1305, and region of interest 1309, as described elsewhere herein.

FIG. 17 illustrates the most conventional approach to prostate cancer treatment defined as the "hemi-gland" margin. Studies have shown that nearly half of cases with apparently unilateral cancer actually had bilateral cancer. In this example, hemi-gland margins of the right or anterior hemisphere would both have failed, indicating the need for a more comprehensive and patient-specific cancer detection and treatment approach.

Figure 18:
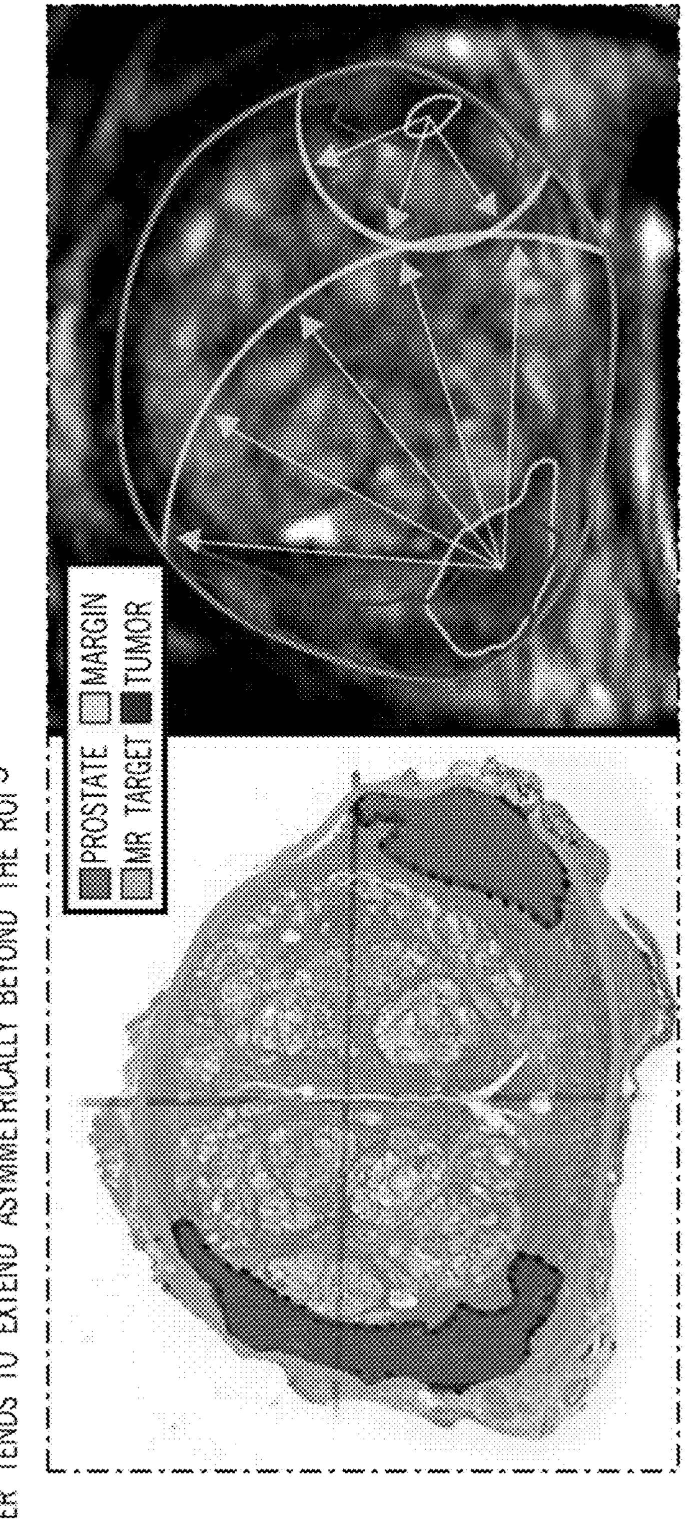
FIG. 18 illustrates an isotropic expansion technique.
Figure 19:
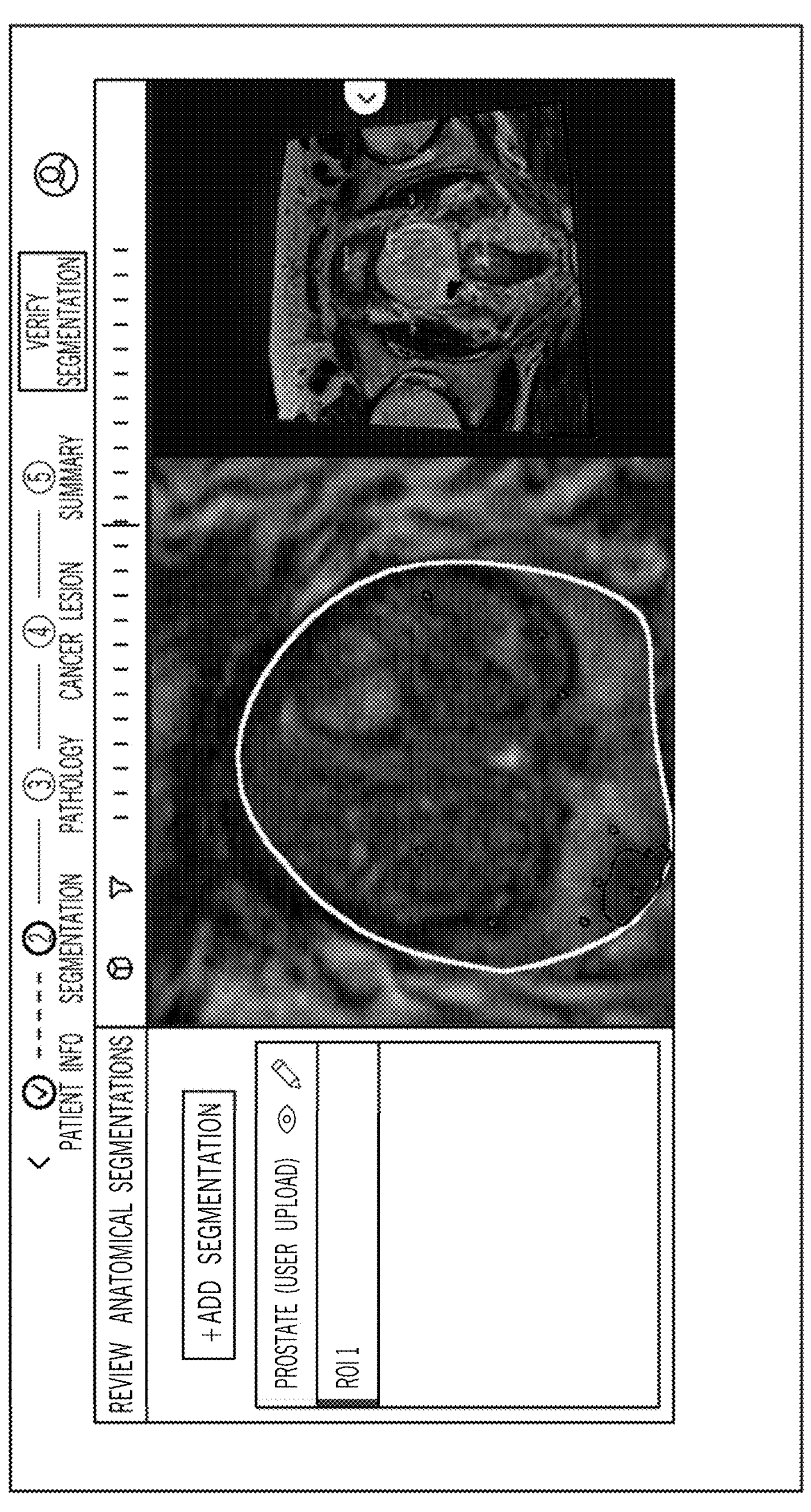
FIG. 19-28 illustrates visual representations and implementations of a software and user interface for mapping cancer using a machine learning algorithm.
Figure 20:
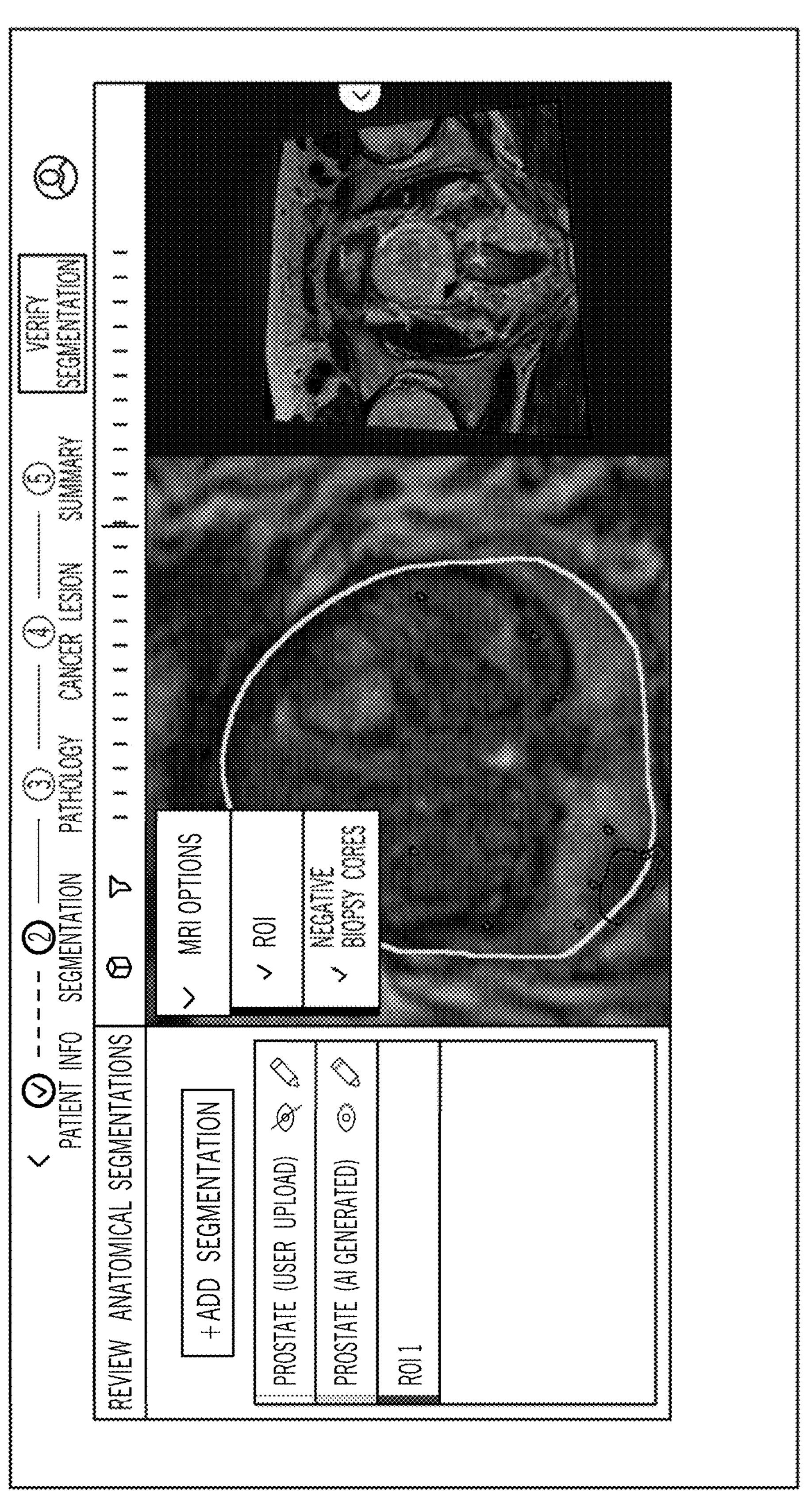
Figure 21:
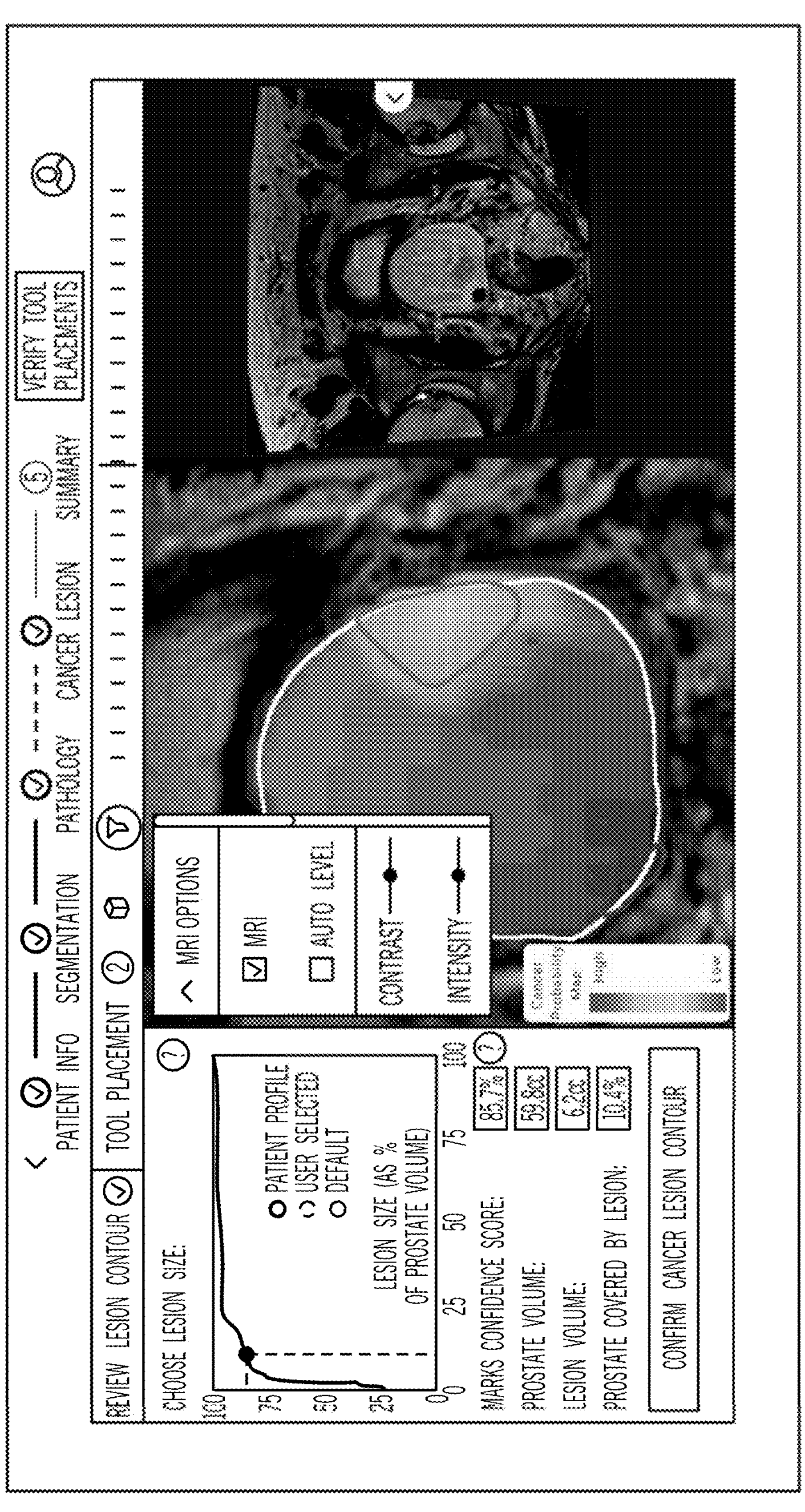
Figure 22:
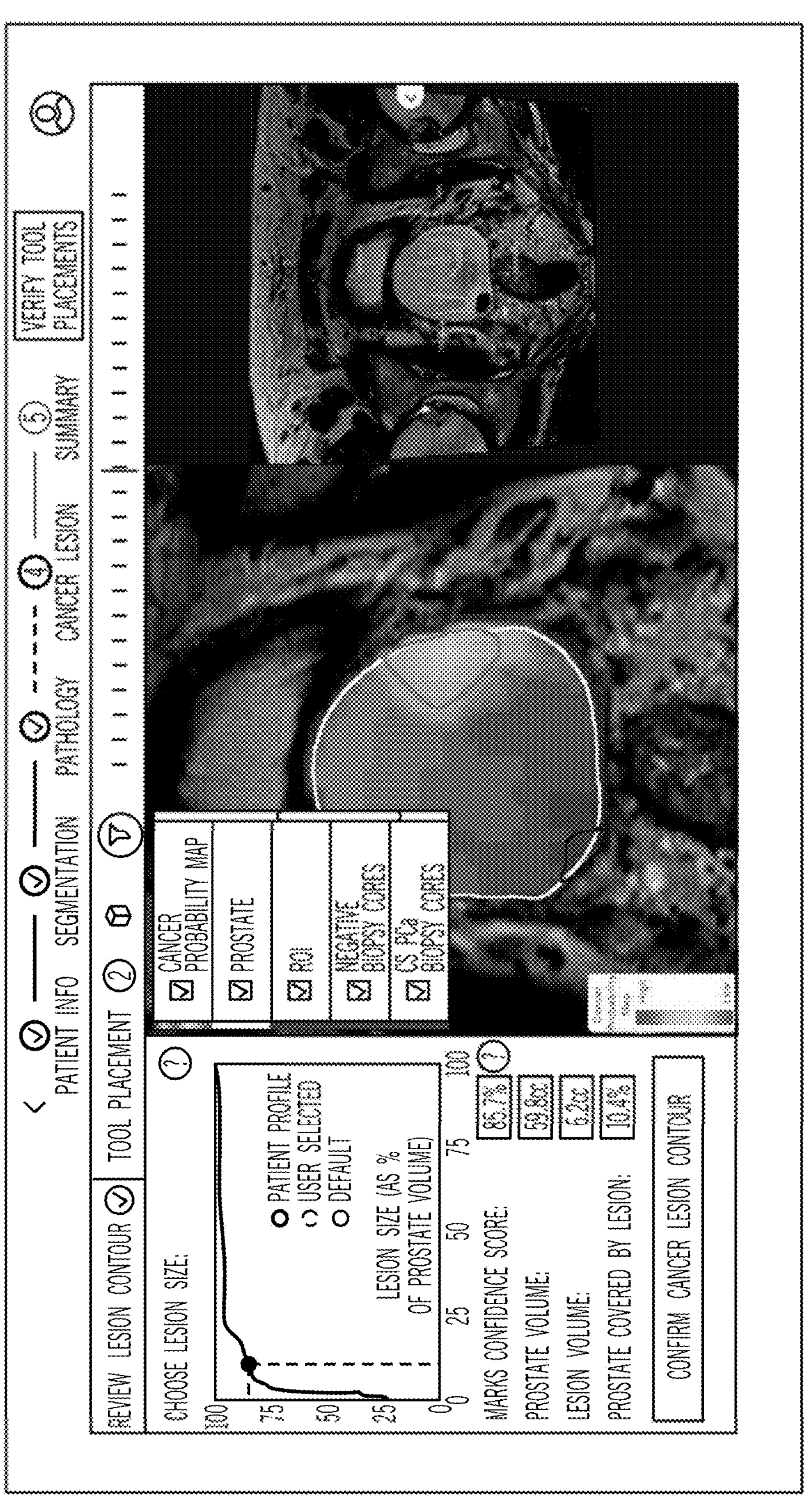
Figure 23:
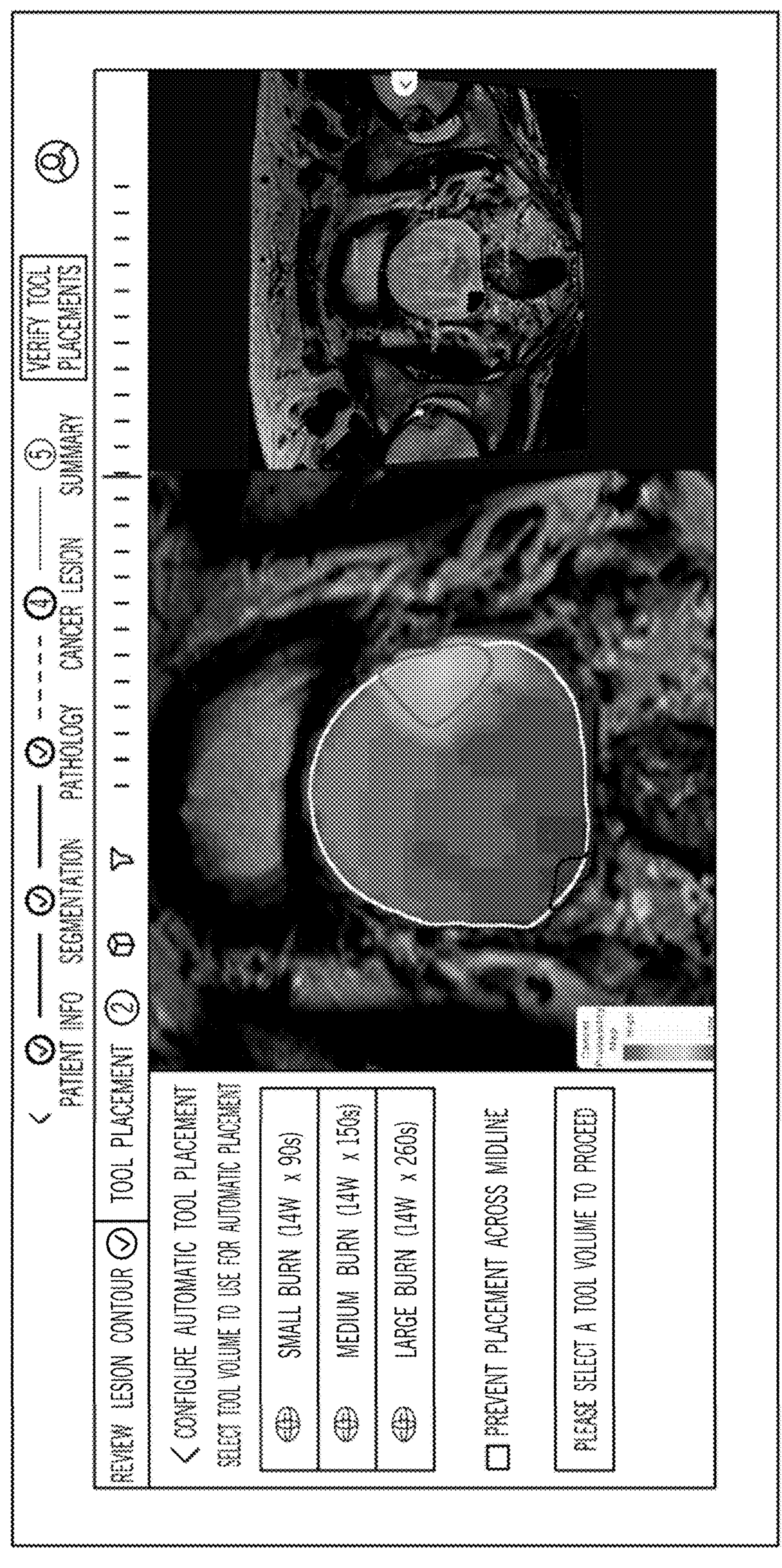
Figure 24:
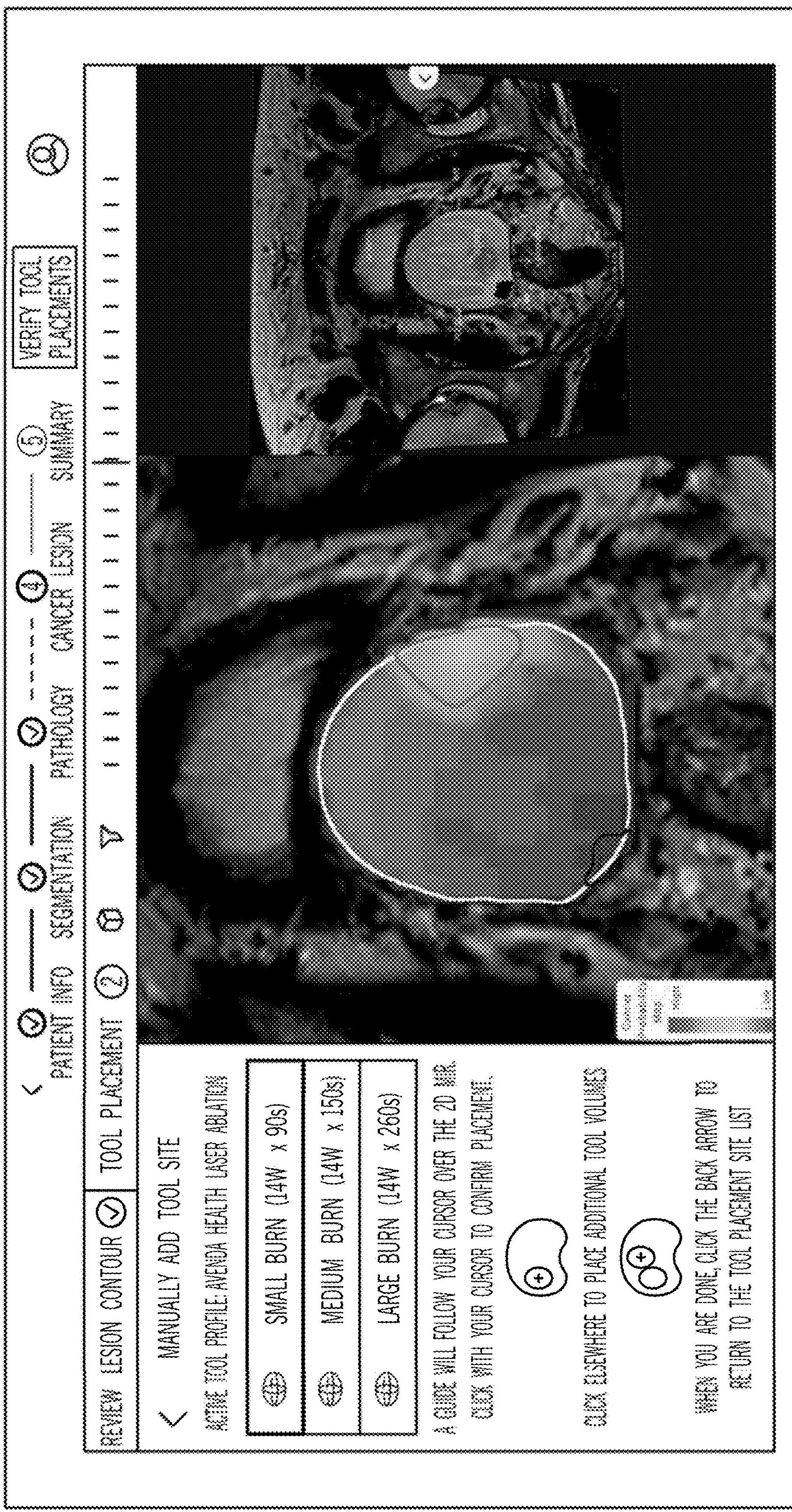
Figure 25:
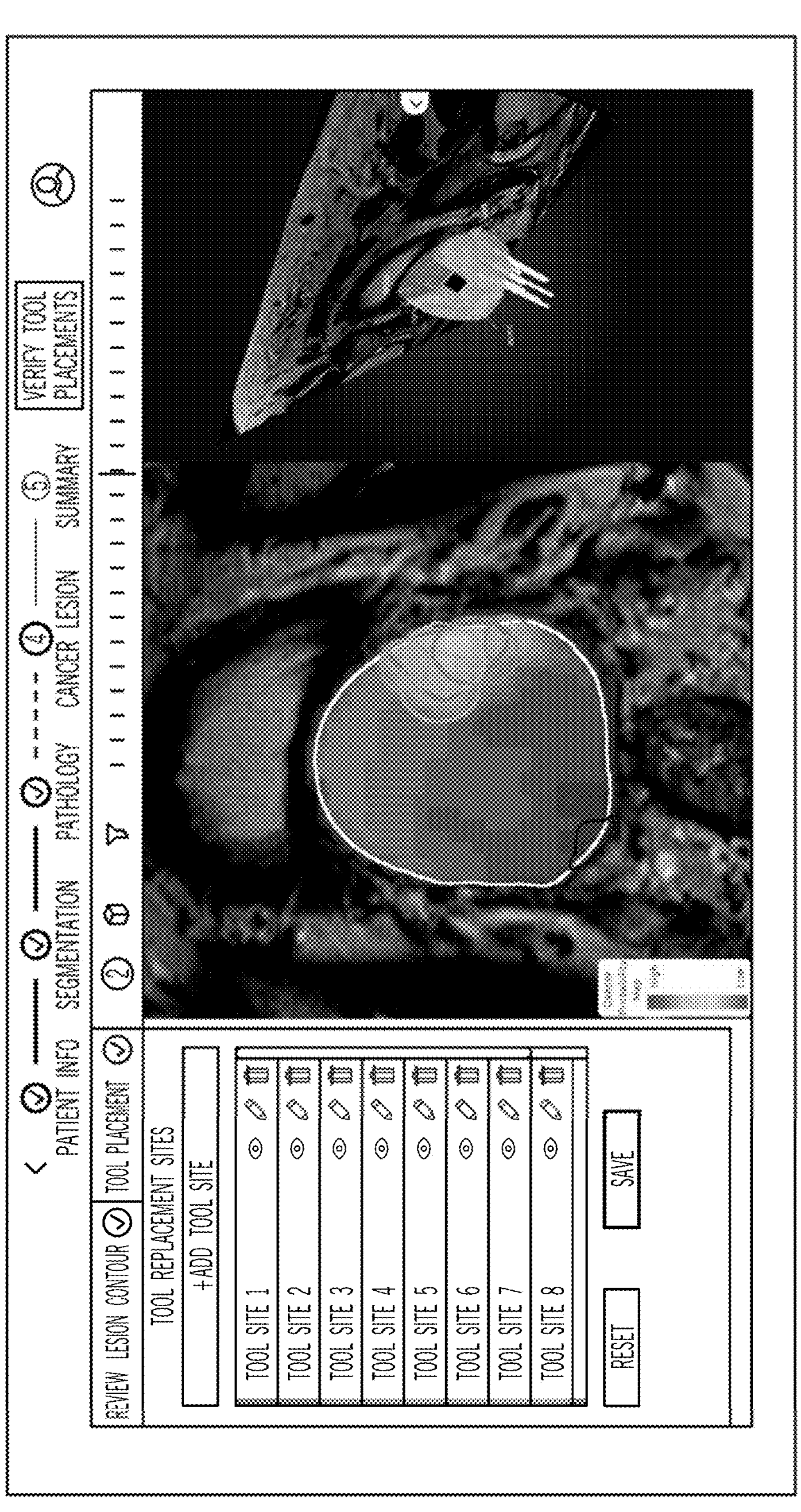
Figure 26:
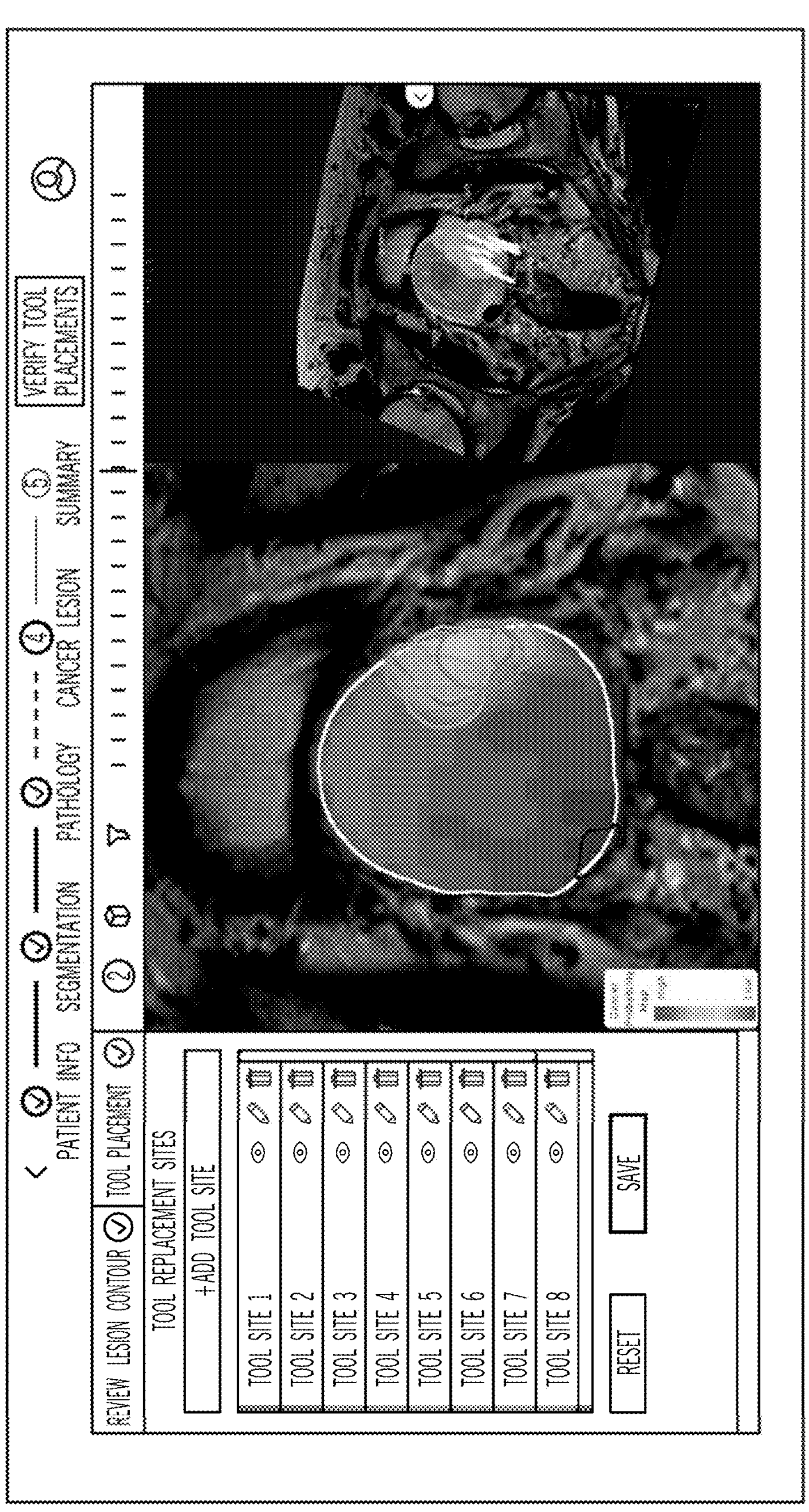
Figure 27:
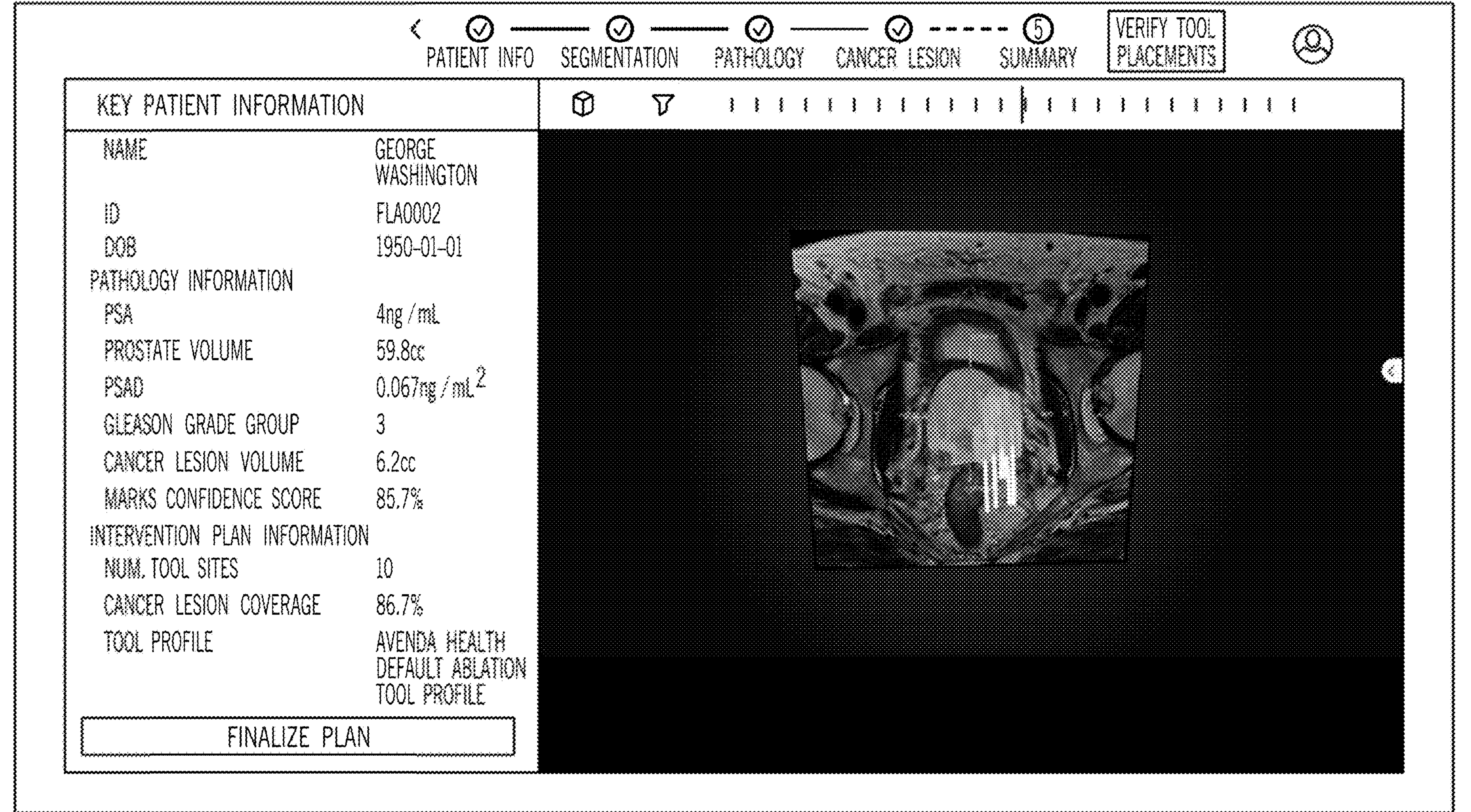
Figure 28:
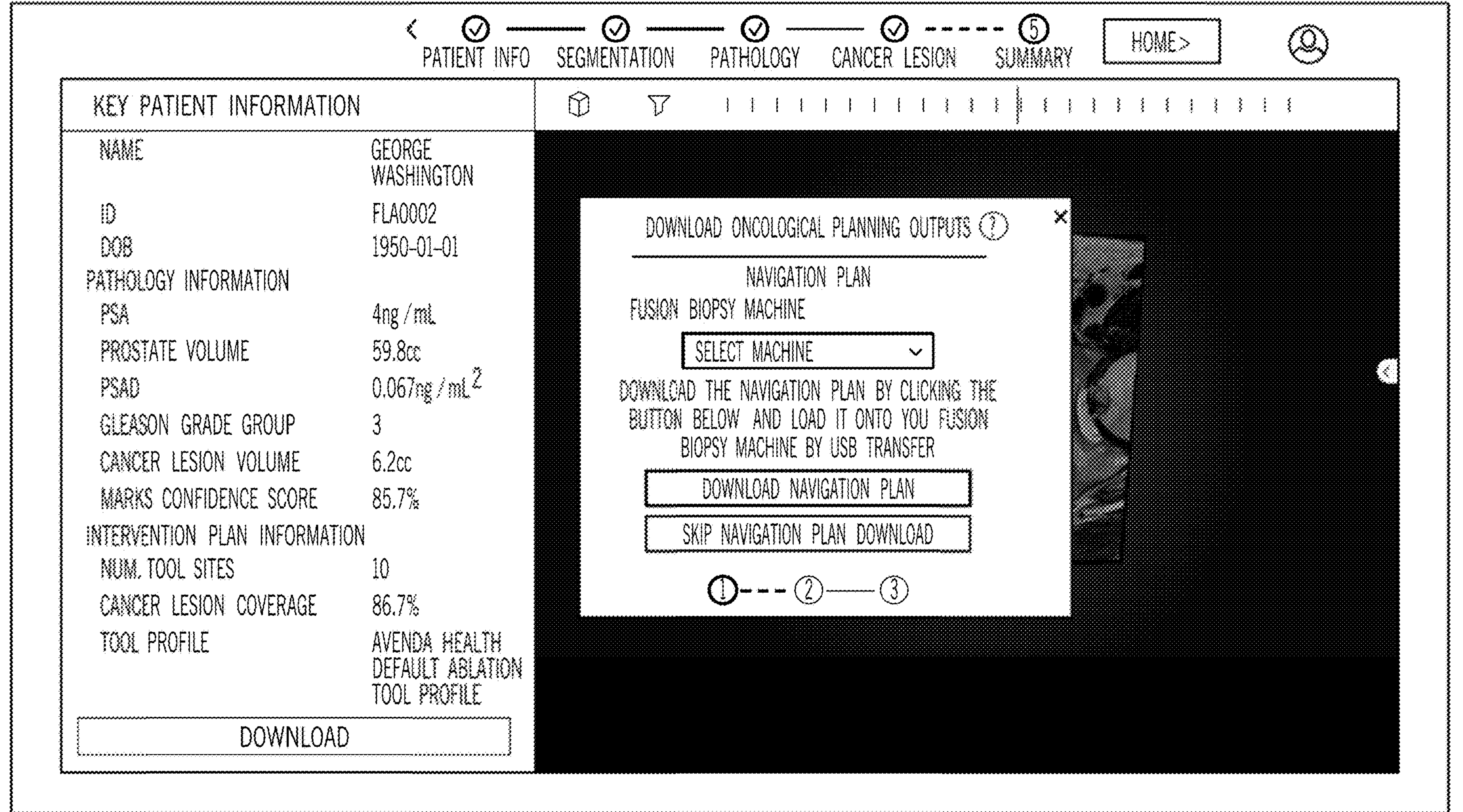

FIG. 18 illustrates another conventional approach to prostate cancer detection and treatment defined as the isotropic region of interest (ROI) expansion approach. The approach defines a uniform, or isotropic, margin around the ROI. However, this approach fails to account for the unpredictable and asymmetric way MIR-invisible tumor extensions often grow, indicating the need for a more comprehensive and patient-specific cancer detection and treatment approach.

FIGS. 19-28 illustrate various visual representations and implementations of a software and user interface for mapping cancer using a machine learning algorithm, as discussed above.

The articles "a," "an," and "the" are intended to mean that there are one or more of the elements in the preceding descriptions. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features. Numbers, percentages, ratios, or other values stated herein are intended to include that value, and also other values that are "about" or "approximately" the stated value, as would be appreciated by one of ordinary skill in the art encompassed by embodiments of the present disclosure. A stated value should therefore be interpreted broadly enough to encompass values that are at least close enough to the stated value to perform a desired function or achieve a desired result. The stated values include at least the variation to be expected in a suitable manufacturing or production process, and may include values that are within 5%, within 1%, within 0.1%, or within 0.01% of a stated value.

A person having ordinary skill in the art should realize in view of the present disclosure that equivalent constructions do not depart from the spirit and scope of the present disclosure, and that various changes, substitutions, and alterations may be made to embodiments disclosed herein without departing from the spirit and scope of the present disclosure. Equivalent constructions, including functional "means-plus-function" clauses are intended to cover the structures described herein as performing the recited function, including both structural equivalents that operate in the same manner, and equivalent structures that provide the same function. It is the express intention of the applicant not to invoke means-plus-function or other functional claiming for any claim except for those in which the words 'means for' appear together with an associated function. Each addition, deletion, and modification to the embodiments that falls within the meaning and scope of the claims is to be embraced by the claims.

The terms "approximately," "about," and "substantially" as used herein represent an amount close to the stated amount that still performs a desired function or achieves a desired result. For example, the terms "approximately," "about," and "substantially" may refer to an amount that is within less than 5% of, within less than 1% of, within less than 0.1% of, and within less than 0.01% of a stated amount. Further, it should be understood that any directions or reference frames in the preceding description are merely relative directions or movements. For example, any references to "up" and "down" or "above" or "below" are merely descriptive of the relative position or movement of the related elements.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

What is claimed is:

1. A device for mapping cancer, comprising:

a processor electrically coupled to a memory component storing electronic instructions that, when executed by the processor, cause the device to execute a machine learning algorithm configured to receive inputs and produce an output based on the inputs, wherein:

the inputs comprise data elements from a medical image of a patient; and the output comprises:

an estimate of clinically significant cancer likelihood in the patient; at each voxel of a three-dimensional image;

a lesion contour representing a lesion size of a cancer lesion in the patient; and an encapsulation confidence score representing an estimated likelihood that the lesion contour encompasses all clinically significant prostate cancer in the patient.

2. The device of claim 1, wherein:

the inputs further comprise at least one of prostate specific antigen (PSA) or fusion based biopsy data.

3. The device of claim 1, wherein the output further comprises at least one of a cancer estimation map (CEM), an estimate of cancer stage, or an estimated likelihood of extracapsular extension (ECE).

4. The device of claim 3, wherein the CEM illustrates a color-coded heat map representing a likelihood of cancer at each voxel of the three-dimensional image.

5. The device of claim 1, wherein the medical image is an MRI image of a patient's anatomy.

6. The device of claim 5, wherein the anatomy includes a prostate.

7. The device of claim 1, wherein the output further comprises a visual curve representing the encapsulation confidence score versus the lesion size.

8. The device of claim 7, wherein the visual curve includes a point representing a certain lesion size and a certain encapsulation confidence score.

9. The device of claim 8, wherein the point is configured to be visually manipulated along the visual curve to change the certain lesion size and the certain encapsulation confidence score represented by the point.

10. The device of claim 9, wherein manipulating the point alters the lesion contour.

11. The device of claim 1, wherein the medical image includes an MRI image.

12. A method for mapping cancer, comprising:

inputting data elements from medical images of a patient into a machine learning model estimating a likelihood of clinically significant cancer in a patient; and generating an output, via the machine learning model, including an estimate of the clinically significant cancer likelihood at each voxel of a three-dimensional image, the output further comprising:

an adjustable lesion contour representing at least one of a size of a cancer lesion or a margin determination for the cancer lesion in the patient; and an encapsulation confidence score representing a probability of all clinically significant prostate cancer in the patient being within a specified lesion contour.

13. The method of claim 12, further comprising inputting data elements from at least one of a biopsy, biopsy pathology labels, or fusion based biopsy data into the machine learning model.

14. The method of claim 12, wherein the machine learning model is trained on a population data set including the data elements.

15. The method of claim 12, wherein the output includes a visual representation of the three-dimensional image with a color-coded heat map representing the clinically significant cancer likelihood at each voxel.

16. A method for mapping cancer, comprising:

inputting data elements from medical images of a patient into a machine learning model estimating a likelihood of clinically significant cancer in the patient; and displaying a visual representation of the likelihood at each voxel of a three-dimensional image, the visual representation comprising:

a cancer estimation map (CEM) illustrating a color-coded heat map representing the likelihood of clinically significant cancer overlying the image, the CEM including a lesion contour representing a size of a cancer lesion; and a curve representing an encapsulation confidence score versus the lesion size, the curve including a point representing the lesion size and the encapsulation confidence score;

wherein:

the point is configured to be visually manipulated along the curve to change the lesion size and the encapsulation confidence score represented by the point; and manipulating the point alters the lesion contour.

17. The method of claim 16, further including displaying an interventional instrument in a position relative to the image.

18. The method of claim 17, wherein a position of the interventional instrument is configured to be altered relative to the image.

19. The method of claim 17, further comprising displaying a location of a biopsy core overlying the image.

* * * * *